United States Patent
Kaihatsu et al.

(10) Patent No.: US 9,801,850 B2
(45) Date of Patent: Oct. 31, 2017

(54) ANTIBACTERIAL AGENT

(75) Inventors: Kunihiro Kaihatsu, Suita (JP); Yoshimi Matsumoto, Suita (JP)

(73) Assignee: OSAKA UNIVERSITY, Osaka (JP)

( * ) Notice: Subject to any disclaimer, the term of this patent is extended or adjusted under 35 U.S.C. 154(b) by 0 days.

(21) Appl. No.: 13/388,015

(22) PCT Filed: Jul. 30, 2010

(86) PCT No.: PCT/JP2010/062952
§ 371 (c)(1),
(2), (4) Date: Jan. 30, 2012

(87) PCT Pub. No.: WO2011/013825
PCT Pub. Date: Feb. 3, 2011

(65) Prior Publication Data
US 2012/0136049 A1    May 31, 2012

(30) Foreign Application Priority Data

Jul. 31, 2009  (JP) .................................. 2009-178747

(51) Int. Cl.
*A61K 31/35*       (2006.01)
*A61P 31/04*       (2006.01)
*C07D 311/74*      (2006.01)
*A61K 31/353*      (2006.01)
*A01N 43/16*       (2006.01)

(52) U.S. Cl.
CPC ............ *A61K 31/353* (2013.01); *A01N 43/16* (2013.01)

(58) Field of Classification Search
None
See application file for complete search history.

(56) References Cited

U.S. PATENT DOCUMENTS

| | | | |
|---|---|---|---|
| 5,137,922 A | 8/1992 | Shimamura et al. | |
| 2006/0041010 A1 | 2/2006 | Chan et al. | |
| 2006/0134286 A1 | 6/2006 | Maeda | |
| 2006/0148726 A1* | 7/2006 | Berg ............................ | 514/27 |
| 2008/0058409 A1 | 3/2008 | Fukami et al. | |
| 2011/0003889 A1 | 1/2011 | Kaihatsu et al. | |

FOREIGN PATENT DOCUMENTS

| | | |
|---|---|---|
| CN | 1231277 | 10/1999 |
| CN | 1650856 | 8/2005 |
| JP | 3-101623 | 4/1991 |
| JP | 2001-253879 | 9/2001 |
| JP | 2002-255810 | 9/2002 |
| JP | 2006-525796 | 11/2006 |
| JP | 2009-084266 | 4/2009 |
| WO | 03/094878 | 11/2003 |
| WO | 2004/076621 | 9/2004 |
| WO | 2006/021888 | 3/2006 |
| WO | 2006/080328 | 8/2006 |
| WO | 2007/105280 | 9/2007 |
| WO | 2009/096581 | 8/2009 |
| WO | 2011/123942 | 10/2011 |

OTHER PUBLICATIONS

Chen et al. "Novel Long-chain-derivative of epigallocatachin-3-O-gallate prepared and purified from green tea polyphenols," Journal of Zhejiang University Science, 2003, vol. 4, No. 6, pp. 714-718.*
Mori et al., Enhanced anti-influenza A virus activity of (−)-epigallocatechin-3-O-gallate fatty acid monoester derivatives: Effect of alkyl chain length, Bioorg. Med. Chem. Lett., 18 4249-4252, 2008.*
Tanaka et al., Synthesis and antioxidant activity of novel amphipathic derivatives of tea polyphenol, Bioorganic & Medicinal Chemistry Letters 8:1801-1806, 1998.*
Zheng et al., Fatty acid synthesis is a target for antibacterial activity of unsaturated fatty acids, FEBS Letters 579:5157-5162, 2005.*
Zhou et al., Mechanism of Synergy between Epigallocatechin Gallate and Beta-Lactams against Methicillin-Resistant, *Staphylococcus aureus*, Antimicrob. Agents Chemother., 45(6):1737-1742, 2001.*

(Continued)

*Primary Examiner* — Kortney L. Klinkel
*Assistant Examiner* — William Y Lee
(74) *Attorney, Agent, or Firm* — Hamre, Schumann, Mueller & Larson, P.C.

(57) ABSTRACT

The present invention provides an epigallocatechin gallate derivative (EGCG derivative) that has excellent safety and antibacterial properties. An epigallocatechin gallate derivative represented by the following chemical formula (1), an isomer thereof, or a salt thereof is used as an antibacterial agent. In the formula, $R^1$ to $R^6$ are each a hydrogen atom, halogen, sodium, potassium, or a straight-chain or branched, saturated or unsaturated acyl group and may be identical to or different from one another. The acyl group may be substituted further with one or more substituents. At least one of the $R^1$ to $R^6$ is the acyl group. $R^7$ to $R^{16}$ are each a hydrogen atom, halogen, sodium, or potassium and may be identical to or different from one another.

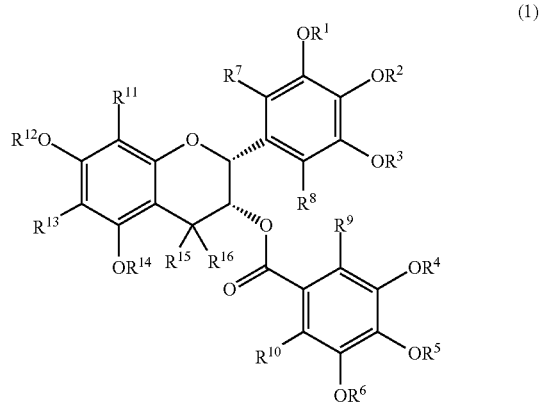

(1)

9 Claims, 3 Drawing Sheets

(56) References Cited

OTHER PUBLICATIONS

Osterburg et al., Highly antibiotic-resistant Acinetobacter baumannii clinical isolates are killed by the green tea polyphenol (−) epigallocatechin-3-gallate (EGCG), Clinical Microbiology and Infection, 15(4):341-346 , 2009.*

Matsumura, et al., "Enhanced antitumor activities of (−)-epigallocatechin-3-O-gallate fatty acid monoester derivatives in vitro and in vivo", Biochemical and Biophysical Research Communications, vol. 377, No. 4, pp. 1118-1122, 2008.

Chen, et al., "Preparation, structure and antioxidant activity of EGCG palmitate", Journal of Zhejiang University (Science Edition), vol. 30, No. 4, pp. 422-425, 2003.

Toda et al., "Antibacterial and anti-hemolysin activities of tea catechins and their structural relatives", Japanese Journal of Bacteriology, 45 (2) , 561-566, 1990—English Abstract on p. 566.

Hu et al., "Epigallocatechin Gallate Synergistically Enhances the Activity of Carbapenems against Methicillin-Resistant *Staphylococcus aureus*", Antimicrob. Agents Chemother., 46(2), 558-560, 2002.

Zhao et al., "Mechanism of Synergy between Epigallocatechin Gallate and β-Lactams against Methicillin-Resistant *Staphylococcus aureus*", Antimicrob. Agents Chemother., 45(6), 1737-1742, 2001.

Yanagawa et al., "A Combination Effect of Epigallocatechin Gallate, a Major Compound of Green Tea Catechins, with Antibiotics on Helicobacter pylori Growth In Vitro", Curr. Microbiol., 47, 244-249, 2003.

Hatano et al., "Enhancement of antibacterial effects of epigallocatechin gallate, using ascorbic acid", Phytochemistry, 69, 3111-3116, 2008.

Kida et al., "Identification of Biliary Metabolites of (−)-Epicallocatechin Gallate in Rats", J. Agric. Food Chem., 48, 4151-4155, 2000.

Tanaka et al., "Synthesis and Antioxidant Activity of Novel Amphipathic Derivatives of Tea Polyphenol",. Bioorg. Med. Chem. Lett., 8, 1801-1806, 1998.

Mori et al., "Enhanced anti-influenza A virus activity of (−)-epigallocatechin-3-O-gallate fatty acid monoester derivatives: Effect of alkyl chain length", Bioorg. Med. Chem. Lett., 18, 4249-4252, 2008.

Utenova et al., "Antioxidant activity of O-protected derivatives of (−)-epigallocatechin-3-gallate: inhibition of soybean and rabbit 15-lipoxygenases", ARKIVOC, 9, 6-16, 2007.

Fudoji et al., "Research on Development of Lipophilic Catechin Derivatives (2) ~ Development of Synthesis Method, and Radical Scavenging Activity and Antibacterial Activity ~", Abstracts of Scientific Presentation in the 129th Annual Meeting of the Pharma—partial translation.

Zlydnikov et al, "Study of rimantadine in the USSR: a review of the literature", Rev Infect Dis, 3(3): 408-421, 1981; Abstract Only.

Duff et al, "The transmembrane domain of influenza A M2 protein forms amantadine-sensitive proton channels in planar lipid bilayers" Virology, 190(1):485-489, 1992; Abstract Only.

Woods et al, "4-Guanidino-2,4-Dideoxy-2,3-Dehydro-N-Acetylneuraminic Acid Is a Highly Effective Inhibitor Both of the Sialidase (Neuraminidase) and of Growth of a Wide Range of Influenza A and B Viruses In Vitro", Antimicrob Agents Chemother, 37(7): 147.

von Itzstein et al, "Rational design of potent sialidase-based inhibitors of influenza virus replication", Nature, 363(6428): 418-423, 1993; Abstract Only.

Kim et al, "Influenza neuraminidase inhibitors possessing a novel hydrophobic interaction in the enzyme active site: design, synthesis, and structual analysis of carbocyclic sialic acid analogues with potent anti-influenza activity" J Am Chem Soc, 119(4).

Lam et al, "A potential prodrug for a green tea polyphenol proteasome inhibitor: evaluation of the peracetate ester of (−)-epigallocatechin gallate [(−)-EGCG]", Bioorg Med Chem, 12(21): 5587-5593, 2004.

Chen, et al., "A novel long-chain acyl-derivative of epigallocatechin-3-O-gallate prepared and purified from green tea polyphenols", Journal of Zhejiang University Science, 2003, vol. 4, No. 6, pp. 714-718.

Zaitseva, et al., "Class II fusion protein of alphaviruses drves membrane fusion through the same pathway as class I protein", The Journal of Cell Biology, 2005, vol. 169, No. 3, pp. 167-177.

Harrison, "Viral Membrane Fusion", Nat. Struct. Mol. Biol., Jul. 2008, vol. 15, No. 7, pp. 690-698.

Office Action issued in co-pending U.S. Appl. No. 14/581,543, dated Mar. 13, 2017, 10 pages.

* cited by examiner

ANTIBACTERIAL AGENT

TECHNICAL FIELD

The present invention relates to an antibacterial agent.

BACKGROUND ART

Epigallocatechin gallate (hereinafter referred to as EGCG) is one kind of catechin extracted from tea leaves, and is attracting attention as a beneficial natural product having an antibacterial effect (Non-Patent Documents 1 to 7). In particular, EGCG has excellent safety because it is naturally derived, and is expected to come into use as an antibacterial agent.

However, for practical realization of such an antibacterial agent, it is desired that the antibacterial effect of EGCG be improved still further.

CITATION LIST

Non-Patent Document(s)

Non-Patent Document 1: Masako TODA et al., Nippon Saikingaku Zasshi (Japanese Journal of Bacteriology), 45(2) 563, 1990

Non-Patent Document 2: Zhao W-H., et al., Antimicrob, Agents Chemother. Vol. 46: pp. 588-560, 2002

Non-Patent Document 3: Zhao W-H., et al., Antimicrob, Agents Chemother. Vol. 45: pp. 1737-1742, 2001

Non-Patent Document 4: Yanagawa Y., et al., Curr. Microbiol. Vol. 47: pp. 244-249, 2003

Non-Patent Document 5: Hatano T., et al., Phytochemistry, Vol. 69, pp. 3111-3116, 2008

Non-Patent Document 6: K. Kida, et al., J. Agric. Food Chem. Vol. 48, pp. 4151-4155, 2000

Non-Patent Document 7: T. Tanaka, et al., Bioorg. Med. Chem. Lett. Vol. 8, pp. 1801-1806, 1998

BRIEF SUMMARY OF THE INVENTION

Problem to be Solved by the Invention

With the foregoing in mind, it is an object of the present invention to provide novel EGCG derivatives having excellent safety and antibacterial properties.

Means for Solving Problem

In order to achieve the above object, the present invention provides an antibacterial agent containing an epigallocatechin gallate (EGCG) derivative represented by the following chemical formula (1), an isomer thereof, or a salt thereof.

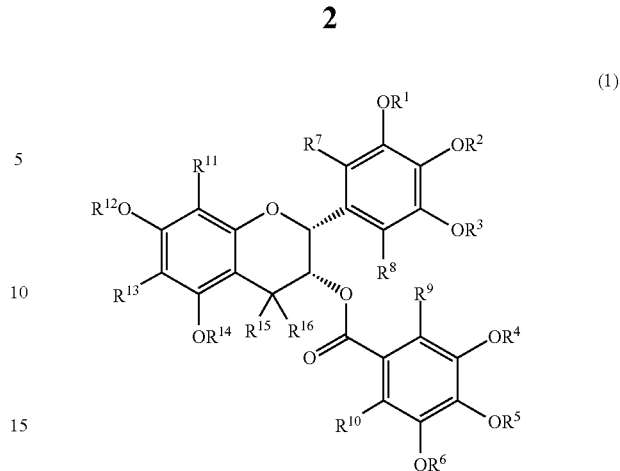

(1)

In the chemical formula (1), $R^1$ to $R^6$ are each a hydrogen atom, halogen, sodium, potassium, or a straight-chain or branched, saturated or unsaturated acyl group and may be identical to or different from one another. The acyl group may be substituted further with one or more substituents. At least one of $R^1$ to $R^6$ is the acyl group. $R^7$ to $R^{16}$ are each a hydrogen atom, halogen, sodium, or potassium and may be identical to or different from one another.

Effects of the Invention

According to the present invention, it is possible to inhibit bacterial infection with excellent stability and antibacterial properties.

MODE FOR CARRYING OUT THE INVENTION

Figure 1:
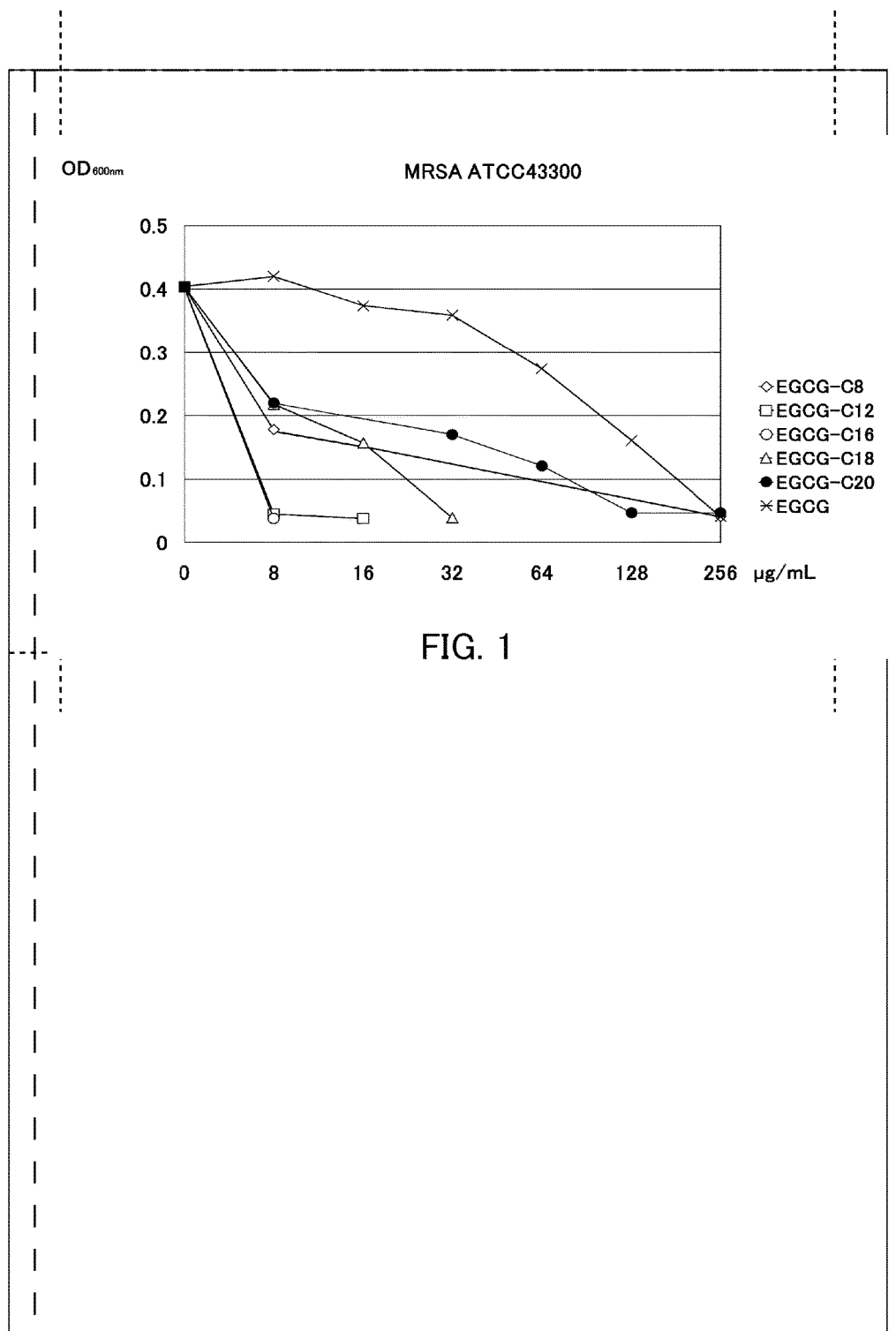
FIG. 1 is a graph showing the antibacterial effect of EGCG derivatives against MRSA in Example 1 of the present invention.

In the present invention, the term "antibacterial" means inhibiting the propagation of bacteria, which may be either the inhibition of the propagation by a bactericidal action (killing the bacteria) or by a bacteriostatic action (inhibiting the growth of the bacteria), for example.

As described above, the antibacterial agent according to the present invention contains an epigallocatechin gallate derivative represented by the following chemical formula (1), an isomer thereof, or a salt thereof.

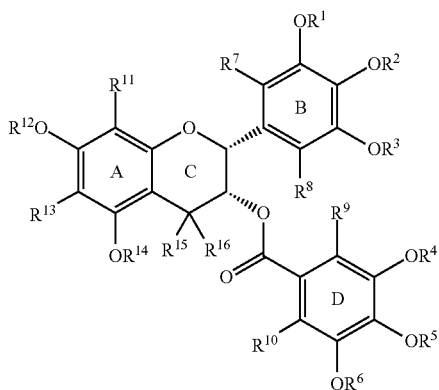

(1)

In the chemical formula (1), $R^1$ to $R^6$ are each a hydrogen atom, halogen, sodium, potassium, or a straight-chain or branched, saturated or unsaturated acyl group and may be identical to or different from one another. The acyl group may be substituted further with one or more substituents. At least one of the $R^1$ to $R^6$ is the acyl group. $R^7$ to $R^{16}$ are each a hydrogen atom, halogen, sodium, or potassium and may be identical to or different from one another. Sodium or potassium each may be any of other monovalent metals or alkali metals.

In the chemical formula (1), A, B, C, and D represent respective rings in EGCG. In the present invention, hereinafter, epigallocatechin gallate is referred to as "EGCG", and a derivative of EGCG is referred to as an "EGCG derivative".

In the present invention, the EGCG derivative encompasses, for example: compounds represented by the chemical formula (1); salts thereof; isomers, such as tautomers, stereoisomers, optical isomers, and geometric isomers, thereof; and mixtures of isomers. The salts are not particularly limited, and examples thereof include inorganic acid salts, organic acid salts, inorganic basic salts, organic basic salts, and acidic or basic amino acid salts. The isomers can be purified by, for example, conventionally known separation methods such as various kinds of chromatography. Furthermore, in the present invention, the EGCG derivative also encompasses, for example, compounds produced through metabolism, such as oxidation, reduction, hydrolysis, or conjugation, of the compounds represented by the chemical formula (1).

In $R^1$ to $R^6$, the main chain length of the acyl group is not particularly limited. For example, the main chain length of the acyl group is 2 to 20 atoms, preferably 4 to 20 atoms, more preferably 8 to 18 atoms, and still more preferably 12 to 16 atoms, including a carbon atom of a carbonyl group. It is to be noted that the main chain length of the acyl group refers to the number of atoms in the longest chain of the acyl group, for example, and not only a carbon atom but also a nitrogen atom, a sulfur atom, a phosphorus atom, an oxygen atom, a boron atom, a halogen atom, and the like may be contained therein. Moreover, in the antibacterial agent of the present invention, EGCG as the basic skeleton of the EGCG derivative is, for example, catechin contained in tea and the like, and it is well known that catechin has excellent safety. Also, the acyl group(s) of $R^1$ to $R^6$ has excellent safety. Therefore, it can be expected that the antibacterial agent of the present invention is a pharmaceutical composition that also has excellent safety.

In $R^1$ to $R^6$, the number of carbon atoms in the acyl group is not particularly limited. For example, the acyl group contains 2 to 20 carbon atoms, preferably 4 to 20 carbon atoms, more preferably 8 to 18 carbon atoms, and still more preferably 12 to 16 carbon atoms, including a carbon atom of a carbonyl group. The number of carbon atoms preferably is 4, 8, 12, 16, 18, or 20, more preferably 8, 12, 16, 18, or 20, still more preferably 16, 18, or 20, and particularly preferably 16 or 18, for example. When the acyl group further is substituted with the above-described substituent, it is preferable that the number of carbon atoms is, for example, the number excluding the number of carbon atoms in the substituent. Furthermore, the unsaturated acyl group may be either cis or trans, for example.

The acyl group is not particularly limited, and examples thereof include a formyl group (C1), an acetyl group (C2), a propionyl group (C3), a butyryl group (C4), an isobutyryl group (C4), a valeryl group (C5), an isovaleryl group (C5), a pivaloyl group (C5), a hexanoyl group (C6), an octanoyl group (C8), a geranoyl group (3,7-dimethylocta-2,6-dienoyl group) (C10), a trans-8-methyl-6-nonenoyl group (C10), an undecanoyl group (C11), a lauroyl group (dodecanoyl group) (C12), a tridecanoyl group (C13), a 12-(dimethylamino)lauroyl group (12-(dimethylamino)dodecanoyl group) (C14), a farnesoyl group (3,7,11-trimethyldodeca-2,6,10-trienoyl group) (C15), a palmitoyl group (hexadecanoyl group) (C16), a palmitoleyl group (C16), a heptadecanoyl group (C17), a stearoyl group (octadecanoyl group) (C18), an oleoyl group (C18), a linoleyl group (C18), a linolenyl group (C18), a nonadecanoyl group (C19), and an eicosanoyl group (icosanoyl group) (C20). Note here that the "C" in parentheses after each of the acyl groups listed above indicates the number of carbon atoms, including a carbon atom of a carbonyl group.

Among the above-listed acyl groups, for example, acyl groups represented by the following chemical formulae, and the like are particularly preferable. In the following chemical formulae, the position of the unsaturated bond is not limited to those shown in the formulae. Specifically, for example, the unsaturated bond (double bond) in a trans-8-methylnonenoyl group (C10) is not limited to the 6-position shown in the formula below and may be any of the 2- to 5-positions and the 7-position, for example.

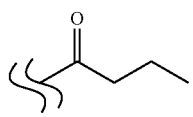

butyryl group (C4)

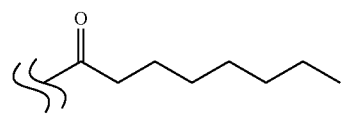

octanoyl group (C8)

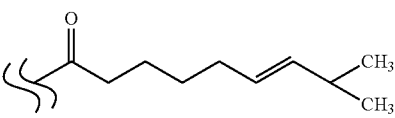

trans-8-methyl-6-nonenoyl group (C10)

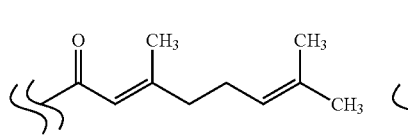
geranoyl group (C10)

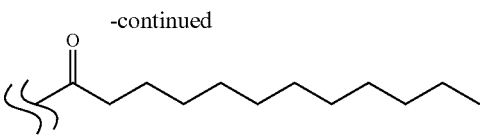
lauroyl group (C12)

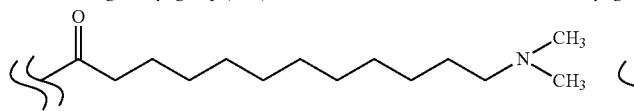
12-(dimethylamino)lauroyl group (C14)

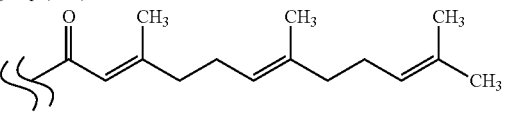
farnesoyl group (C15)

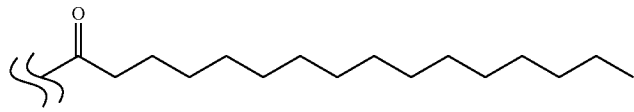
palmitoyl group (C16)

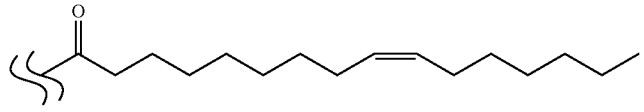
palmitoleyl group (ene: C16)

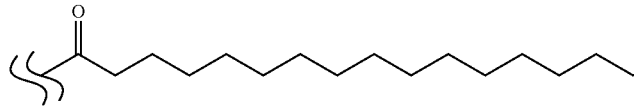
stearoyl group (C18)

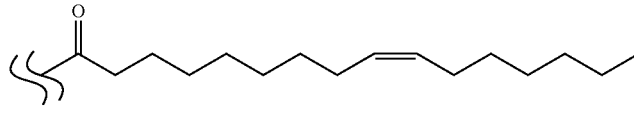
oleoyl group (ene: C18)

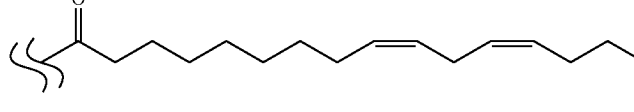
linoleyl group (diene: C18)

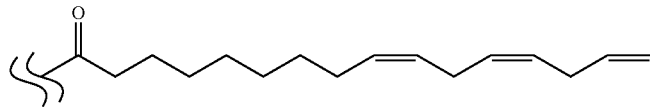
linolenyl group (triene: C18)

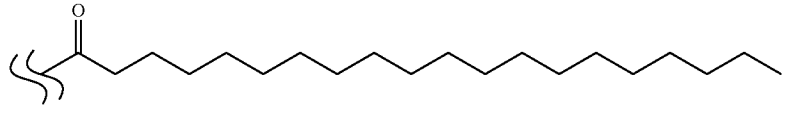
eicosanoyl group (C20)

The kind of the acyl group is not particularly limited, and as described above, the acyl group may be either an unsaturated acyl group or a saturated acyl group. Among them, the unsaturated acyl group is preferable between the unsaturated acyl group and the saturated acyl group having the same main chain length, and it is preferable that the number of unsaturated bonds therein is large, for example. The number of unsaturated bonds in the acyl group is not particularly limited, and is, for example, 1 to 3, preferably 2 to 3.

In $R^1$ to $R^6$, when the acyl group is substituted further with the substituent, the substituent is not particularly limited. The substituent may be an alkyl group, an amino group, an alkylamino group, a dialkylamino group, or the like.

The alkyl group may be, for example, a straight-chain or branched alkyl group having 1 to 6 carbon atoms and preferably is a methyl group. Furthermore, an alkyl group in the alkylamino group may be, for example, a straight-chain or branched alkyl group having 1 to 6 carbon atoms and preferably is a methylamino group. An alkyl group in the dialkylamino group may be, for example, a straight-chain or branched alkyl group having 1 to 6 carbon atoms and preferably is a dimethylamino group. They may be identical to or different from one another.

In the chemical formula (1), two or more of $R^1$ to $R^6$ may be the acyl groups, or only one of them may be the acyl group, for example. In the former case, the acyl groups at the respective positions may be identical to or different from one another, for example. When two or more of $R^1$ to $R^6$ are the acyl groups, each of the acyl groups preferably has a main chain length of 4 to 12 carbon atoms, more preferably 4 to 8 carbon atoms, for example. Rs other than the acyl groups are not particularly limited, and preferably are hydrogen atoms, for example.

In the chemical formula (1), among $R^1$ to $R^6$, the acyl group position(s) is not particularly limited. In the chemical formula (1), for example, it is preferable that at least one of $R^1$ and $R^2$ in the B ring and $R^5$ and $R^6$ in the D ring is the acyl group, and it is particularly preferable that any one of $R^1$, $R^2$, $R^5$, and $R^6$ is the acyl group. In this case, Rs other than the acyl group(s) are not particularly limited, and preferably are hydrogen atoms, for example.

In the chemical formula (1), it is preferable that at least one of $R^1$, $R^2$, and $R^3$ in the B ring is the acyl group, and it is more preferable that only one of $R^1$ and $R^2$ in the B ring is the acyl group. EGCG derivatives with a modified B ring have higher metabolic stability, for example.

In the chemical formula (1), as described above, $R^7$ to $R^{16}$ may be identical to or different from one another, and examples thereof other than the acyl group include a hydrogen atom, halogens, sodium, and potassium. As shown in the following chemical formula (2), $R^7$ to $R^{16}$ preferably are hydrogen atoms. In the following formula (2), any of $R^1$ to $R^6$ may be the acyl group, for example. Specifically, for example, it is preferable that at least one of $R^1$ to $R^6$ or any one of $R^1$ to $R^6$ is the above-described acyl group, and it is more preferable that at least one of $R^1$, $R^2$, $R^5$, and $R^6$ or any one of $R^1$, $R^2$, $R^5$, and $R^6$ is the above-described acyl group. Among the acyl groups listed above, for example, a butyryl group, an octanoyl group, a trans-8-methyl-6-nonenoyl group, a geranoyl group, a lauroyl group, a 12-(dimethylamino)lauroyl group, a farnesoyl group, a palmitoyl group, a palmitoleyl group, a stearoyl group, an oleoyl group, a linoleyl group, a linolenyl group, and an eicosanoyl group are preferable.

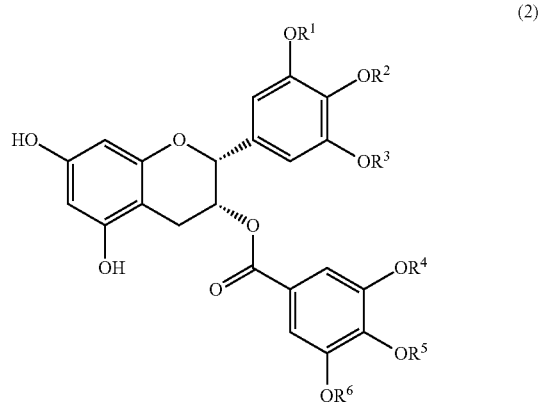

(2)

In the present invention, "halogen" refers to an arbitrary halogen element. Examples of the halogen include fluorine, chlorine, bromine, and iodine. Furthermore, in the present invention, an "alkyl group" is not particularly limited. Examples of the alkyl group include a methyl group, an ethyl group, an n-propyl group, an isopropyl group, n-butyl group, an isobutyl group, a sec-butyl group, a tert-butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, and an icosyl group. The same applies to a group containing an alkyl group in its structure or a group derived from an alkyl group, specifically, e.g., an alkylamino group, a dialkylamino group, an alkoxy group, a carboxyalkyl group, an alkoxycarbonylalkyl group, an alkoxyalkyl group, an alkenoxyalkyl group, or the like.

In the case where a substituent or the like is a group having a chain structure, e.g., an alkyl group, an alkylamino group, a dialkylamino group, an alkoxy group, a carboxyalkyl group, an alkoxycarbonylalkyl group, an alkoxyalkyl group, an alkenoxyalkyl group, or the like, it may have, for example, either a straight-chain or branched structure, unless otherwise limited. The same applies to the case where a chain structure is contained in part of a substituent or the like, e.g., the case where a chain structure is contained in a substituent in a substituted alkyl group, a substituted aryl group, or the like. In the case where a substituent or the like has isomers, the substituent may be, for example, any of the isomers, unless otherwise limited. Specifically, when it is simply referred to as a "propyl group", it may be either an n-propyl group or an isopropyl group, for example. When it is simply referred to as a "butyl group", it may be any of an n-butyl group, an isobutyl group, a sec-butyl group, and a tert-butyl group, for example. When it is simply referred to as a "naphthyl group", it may be either a 1-naphthyl group or a 2-naphthyl group, for example.

In the present invention, for example, only one kind of EGCG derivative may be used, or two or more kinds of EGCG derivatives may be used in combination. In the present invention, for example, two or more kinds of EGCG derivatives having acyl groups at different positions among $R^1$ to $R^6$ may be used, or two or more kinds of EGCG derivatives having different acyl groups may be used. Specifically, it is possible to use a mixture of two or more kinds selected from an EGCG derivative in which $R^1$ in the B ring is the acyl group, an EGCG derivative in which $R^2$ in the B ring is the acyl group, and an EGCG derivative in which $R^3$ in the B ring is the acyl group, or a mixture of all the three kinds of them. It also is possible to use a mixture of two or more kinds selected from an EGCG derivative in which $R^4$ in the D ring is the acyl group, an EGCG derivative in which $R^5$ in the D ring is the acyl group, and an EGCG derivative in which $R^6$ in the D ring is the acyl group, or a mixture of all the three kinds of them. Furthermore, it is also possible to use a mixture of an EGCG derivative in which at least one of $R^4$ to $R^3$ in the B ring is the acyl group and an EGCG derivative in which at least one of $R^4$ to $R^6$ in the D ring is the acyl group.

The antibacterial agent of the present invention is not particularly limited, and can be used against various kinds of bacteria. Examples of the bacteria include Gram-positive bacteria and Gram-negative bacteria. Specific examples of the bacteria include: bacteria of the genus *Bacillus*; bacteria of the genus *Staphylococcus*; bacteria of the genus *Streptococcus*; bacteria of the genus *Enterococcus*; bacteria of the genus *Micrococcus*; bacteria of the genus *Moraxella*; bacteria of the genus *Haemophilis*; *Escherichia coli*; bacteria of the genus *Enterobacter*; bacteria of the genus *Serratia*; bacteria of the genus *Yersinia*; bacteria of the genus *Pseudomonas*; bacteria of the genus *Stenotrophomonas*; bacteria of the genus *Helicobacter*; bacteria of the genus *Campylobacter*; and bacteria of the genus *Legionella*. Examples of the bacteria of the genus *Bacillus* include *B. subtilus* and *B. cereus*. Examples of the bacteria of the genus *Staphylococcus* include staphylococci such as *S. aureus*, *S.*

*epidermidis*, and *S. saprophyticus*. Examples of the *S. aureus* include methicillin-susceptible *Staphylococcus aureus* (MSSA) and methicillin-resistant *Staphylococcus aureus* (MRSA). Examples of the bacteria of the genus *Streptococcus* include streptococci such as *S. pneumoniae, S. pyogenes*, and *S. agalactiae*. Examples of the bacteria of the genus *Enterococcus* include enterococci such as *E. faecalis*. Examples of the bacteria of the genus *Micrococcus* include *M. lutus*. Examples of the bacteria of the genus *Moraxella* include *M. catarhalis*. Examples of the bacteria of the genus *Haemophilis* include *H. influenzae*. Examples of the bacteria of the genus *Enterobacter* include *E. cloacae* and *E. aerogenes*, and examples of the bacteria of the genus *Serratia* include *S. marcescens*. Examples of the bacteria of the genus *Yersinia* include *Y. enterocolitica*. Examples of the bacteria of the genus *Pseudomonas* include *P. aeruginosa* and *P. fluorescens*. Examples of the bacteria of the genus *Stenotrophomonas* include *S. maltophilia*, and examples of the bacteria of the genus *Helicobacter* include *H. pylori*. Examples of the bacteria of the genus *Campylobacter* include *C. jejuni*, and examples of the bacteria of the genus *Legionella* include *L. pneumophila*.

It is only necessary that the antibacterial agent of the present invention contains the EGCG derivative, and the form of the antibacterial agent is by no means limited. The antibacterial agent may be in the form of: liquid such as a solution, a suspension, or a dispersion; solid; powder; or the like, for example. Furthermore, the dosage form is not particularly limited, and can be set as appropriate depending on the administration method, for example. Examples of the dosage form include a liquid medicine, a capsule, a tablet, granules such as microgranules, and a powder medicine. The administration method is not particularly limited, and examples thereof include oral administration and parenteral administration. Examples of the parenteral administration include: transdermal administration; intraperitoneal administration; intravenous administration such as intravenous injection; intramuscular administration; subcutaneous administration such as subcutaneous injection; and rectal administration. Among them, the transdermal administration is preferable. The antibacterial agent of the present invention can be administered as, for example, the EGCG derivative itself or an oral medicine, a sublingual formulation, an eye/nasal drop, a gargle, a topical cream, or the like containing the EGCG derivative, depending on the administration form, for example. The antibacterial agent of the present invention also can be administered as the EGCG derivative itself, or a solution, a suspension, or a dispersion containing the EGCG derivative using a syringe, a nebulizer, an aspirator, or the like. Furthermore, the antibacterial agent of the present invention can be administered as the EGCG derivative itself or powder containing the EGCG derivative using a nebulizer, an aspirator, or the like, for example. Moreover, because the antibacterial agent of the present invention can lower the infectiousness of bacteria, it may be in the form of a cleaner, such as a hand-wash or a wiping agent, containing the EGCG derivative, for example. By treating a place where it is considered that bacteria may be present, e.g., hands, a desk, or the like, with the antibacterial agent of the present invention in such a form, it is possible to lower the infectiousness of the bacteria present in the place so as to prevent bacterial infection. Also, the antibacterial agent of the present invention may be carried in a mask, a filter, or the like, for example.

The antibacterial agent of the present invention can be used for, for example: inhibition and prevention of bacterial infection; and treatment after bacterial infection. Examples of a subject to which the antibacterial agent of the present invention is administered is not particularly limited, and examples thereof include humans and nonhuman animals. Examples of the nonhuman animals include: nonhuman mammals such as pigs, ferrets, rats, mice, and cows; and birds such as ducks and chickens.

In the antibacterial agent of the present invention, the content of the EGCG derivative is not particularly limited, and can be determined as appropriate depending on, for example, the purpose of administering it or its administration method. In the case where the antibacterial agent of the present invention is a gargle, it is preferable that 20 to 100 µmol/l of the EGCG derivative is contained per single dose, for example. In the case where the antibacterial agent of the present invention is an eye/nasal drop, it is preferable that 20 to 100 µmol/l of the EGCG derivative is contained per single dose, for example.

The antibacterial agent of the present invention further may contain an antibacterial substance other than the EGCG derivative, for example.

The antibacterial agent of the present invention further may contain an additive, a base, and the like as appropriate depending on, for example, its dosage form or administration method. Examples of the additive include an excipient, a bonding agent, a lubricant, a disintegrant, a coloring agent, a taste masking agent, an odor masking agent, an emulsifying agent, a surfactant, a solubilizing agent, a suspending agent, a tonicity agent, a buffer, an antiseptic agent, an antioxidant agent, a stabilizing agent, and an absorption promoter. The proportion of each of these additives to be added is not particularly limited. They can be added within the range in which they do not reduce the effect of the EGCG derivative.

The method for producing the EGCG derivative in the present invention is not particularly limited. As the method, a conventionally known method such as an organic synthesis method or a chemical synthesis method utilizing an enzyme or the like can be employed, for example. The chemical synthesis method utilizing an enzyme is not particularly limited, and examples thereof include a method utilizing a lipase, disclosed in WO 2007/105280. This is a method in which an enzyme reaction of EGCG and an acyl group donor as substrates with a lipase is caused in an organic solvent to acylate the EGCG, for example. According to this method, it is possible to acylate EGCG selectively, for example. One example of a method using a lipase will be given below. It should be noted, however, that the present invention is by no means limited by the method for producing an EGCG derivative.

As the lipase, lipase of IUB No. 3.1.1.3. can be used, for example. Specific examples thereof include: lipases derived from the genus *Aspergillus*, such as *Aspergillus niger*; lipases derived from the genus *Candida*, such as *Candida rugosa, Candida cylindracea*, and *Candida antarctica*; lipases derived from the genus *Pseudomonas*, such as *Pseudomonas fluorescens, Pseudomonas cepacia*, and *Pseudomonas stutzeri*; lipases derived from the genus *Alcaligenes*; lipases derived from the genus *Burkholderia*, such as *Burkholderia cepacia*; and lipases derived from porcine pancreas. They can be prepared by conventionally known methods. However, it is also possible to use commercially available products such as, for example, Lipase AS "AMANO", Lipase AYS "AMANO", Lipase PS "AMANO", Lipase AK "AMANO" 20, Lipase AH "AMANO" (all trade names: Amano Enzyme Inc.), Lipase MY, Lipase OF, Lipase PL, Lipase PLC, Lipase PLG, Lipase QLM, Lipase QLC, Lipase QLG, Lipase SL, Lipase TL (all trade names: Meito Sangyo Co., Ltd.), Lipase PPL, L4777 Lipase acrylic resin from *Candida Antarctica*, L3126 Lipase from porcine pancreas (all trade names: Sigma-Aldrich Co.), and the like. The physicochemical properties of the respective commercially available products are as described in their product manuals, and enzymes having similar physicochemical properties also can be used.

Also, the lipase may be the one having physicochemical properties and enzymological properties shown in any one of the following items (1) to (8).

(1) molecular weight: 35,000, isoelectric point: 4.10
   e.g., a lipase derived from *Aspergillus niger*
(2) molecular weight: 64,000, isoelectric point: 4.30, inactivated by the treatment at 80° C. for 10 minutes
   e.g., a lipase derived from *Candida rugosa*
(3) optimum pH: 8, optimum temperature: 60° C., particularly stable at a pH in the range from 4 to 10, particularly stable at 70° C. or lower
   e.g., a lipase derived from *Pseudomonas fluorescens*
(4) molecular weight: 60,000, optimum pH: 6 to 7, pH stability: 3 to 8, optimum temperature: 40° C. to 50° C., particularly stable in the form of a solution at 37° C. or lower
   e.g., a lipase derived from *Candida cylindracea*, a lipase derived from *Candida rugosa*
(5) molecular weight: 30,000, isoelectric point: 4.5, optimum pH: 8 to 9.5, pH stability: 7 to 10, optimum temperature: 50° C., particularly stable at 40° C. or lower
   e.g., a lipase derived from the genus *Alcaligenes*
(6) molecular weight: 31,000, isoelectric point: 4.9, optimum pH: 7 to 9, pH stability: 6 to 10, optimum temperature: 65° C. to 70° C., particularly stable at 50° C. or lower
   e.g., a lipase derived from the genus *Alcaligenes*
(7) molecular weight: 31,000, isoelectric point: 5.2, optimum pH: 7 to 9, pH stability: 6 to 10, optimum temperature: 65° C. to 70° C., particularly stable at 60° C. or lower
   e.g., a lipase derived from *Pseudomonas cepacia*, a lipase derived from *Burkholderia cepacia*
(8) molecular weight: 27,000, isoelectric point: 6.6, optimum pH: 7 to 8, pH stability: 6 to 9, optimum temperature: 50° C., particularly stable at 40° C. or lower
   e.g., a lipase derived from *Pseudomonas stutzeri*

The organic solvent is not particularly limited, and acetonitrile, acetone, dimethylformamide (DMF), dimethyl sulfoxide (DMSO), or the like can be used, for example. Also, the organic solvent may be, for example, an organic solvent with a parameter indicating the hydrophobicity (log P value) in the range from −1.35 to 0.28. Examples of such an organic solvent include the above-described acetonitrile (log P value: −0.45 to 0.19), acetone (log P value: −0.16 to 0.19), DMF (log P value: −1.01 to 0.28), and DMSO (log P value: −1.35 to 0.28). Other than these, conventionally known solvents satisfying the above-described parameter also can be used. Since the log P is a value specific to each solvent, those skilled in the art can select a solvent satisfying the above-described parameter. Note here that the "log P" is a value determined by adding a target substance to a mixed solution of octanol and water, determining the ratio of the concentrations of the target substance in the octanol layer and the concentration of the same in the water layer when the octanol and the water come to equilibrium, and indicating the ratio by common logarithm. As described above, the log P is common as a parameter indicating the hydrophobicity of a substance.

Examples of an acyl group (R—CO—) donor include carboxylic acid vinyl ester (R—CO—O—CH=CH$_2$).

Examples of the acyl group include straight-chain or branched, saturated or unsaturated acyl groups such as described above.

When DMF is used as the organic solvent, the proportion of the added EGCG in a reaction solution of a lipase reaction is not particularly limited, and is, for example, 0.2 to 100 mmol/l, preferably 0.5 to 50 mmol/l, and more preferably 0.5 to 20 mmol/l. The proportion of the added acyl group donor is not particularly limited, and can be determined as appropriate depending on, for example, the proportion of the added EGCG in the reaction solution. Specifically, the proportion (molar ratio) of the added EGCG and acyl group donor is, for example, 1:1 to 1:10, preferably 1:1 to 1:5, and more preferably 1:1 to 1:3. Furthermore, the proportion of the added lipase in the reaction solution can be determined as appropriate depending on, for example, the proportions of the added EGCG and acyl group donor, the specific activity of the lipase, or the like, and is not particularly limited. Specifically, the proportion of the added lipase is 500 to 50,000 U/l, preferably 500 to 5,000 U/l, and more preferably 1,000 to 2,500 U/l with respect to 1 mmol/l of the EGCG, for example.

The conditions for the enzyme reaction are not particularly limited. The reaction temperature is, for example, in the range from 45° C. to 75° C. The reaction time is not particularly limited, and can be determined as appropriate depending on, for example, the amounts of the substrates and the enzyme. The reaction time is, for example, 30 minutes to 24 hours (1440 minutes), preferably 1 hour (60 minutes) to 3 hours (180 minutes), and more preferably 1.5 hours (90 minutes) to 3 hours (180 minutes).

To the reaction solution, a basic catalyst further may be added. Examples of the basic catalyst include pyridine and tertiary amine such as triethylamine. The proportion of the added basic catalyst in the reaction solution is not particularly limited, and is, for example, 5 to 720 mmol/l, preferably 12 to 240 mmol/l, and more preferably 12 to 48 mmol/l.

In EGCG, the position to which the acyl group is introduced can be selected by the kind of the lipase to be used, for example. Furthermore, the number of acyl groups to be introduced into EGCG can be determined by the kind of the organic solvent to be used and the reaction time, for example. Specifically, for example, as the hydrophobicity of the organic solvent becomes relatively higher (as the hydrophilicity of the organic solvent becomes relatively lower), the number of acyl groups to be introduced can be made relatively smaller. On the other hand, as the hydrophilicity of the organic solvent becomes relatively higher (as the hydrophobicity of the organic solvent becomes relatively lower), the number of acyl groups to be introduced can be made relatively larger. Also, for example, by using a mixture of two or more kinds of organic solvents, it is possible to adjust the number of acyl groups to be introduced. Specifically, for example, in the case where one acyl group is to be introduced, acetonitrile or the like preferably is used; for example, in the case where one to two acyl groups are to be introduced, acetone, acetonitrile, or the like preferably is used; and for example, in the case where three to five acyl groups are to be introduced, DMSO, DMF, or the like preferably is used.

Moreover, even when the organic solvent to be used is the same, it is also possible to adjust the number of acyl groups to be introduced by controlling the reaction time and/or the reaction temperature, for example. This will be exemplified below. However, it should be noted that the present invention is not limited thereto. When DMF is used as the organic solvent, by setting the reaction temperature within the range from about 57° C. to about 70° C. and the reaction time to be long, e.g., about 3 to 5 hours, for example, a derivative in which two acyl groups selectively are introduced to EGCG can be obtained preferentially. On the other hand, by lowering the reaction temperature (e.g., to a temperature about 5° C. lower than 57° C.) and shortening the reaction time (e.g., about 1 to 3 hours) as compared to them in the above-described conditions, one acyl group can be introduced selectively. Also, by using a mixed solvent of the same amount (weight) of acetone and DMF, one acyl group can be introduced selectively to EGCG.

Furthermore, the number of acyl groups to be introduced can be increased by adding the above-described basic catalyst to the reaction solution, for example. In this case, the position in EGCG to which an acyl group(s) further is introduced is determined depending on the position selectivity of the lipase, for example, as described above.

The yield of the EGCG derivative by the lipase reaction can be improved relatively by, for example, setting the reaction temperature relatively high. As described above, the reaction temperature generally is 45° C. to 75° C. However, from the viewpoint of improving the yield, it preferably is 57° C. to 75° C., more preferably 57° C. to 70° C. In particular, when the reaction temperature is 57° C. to 70° C., it is possible to realize about 35% to 45% of the yield of the EGCG-acylated derivative, for example. Note here that the yield means, for example, the proportion of an EGCG-acylated derivative (e.g., total monoacylated derivative) calculated assuming that EGCG used in the reaction is 100%. The yield also can be referred to as the conversion efficiency.

In the present invention, as described above, one kind of EGCG derivative may be used or a mixture of two or more kinds of EGCG derivatives may be used, for example. Isolating one kind of EGCG derivative from the mixture can be achieved by, for example, a conventionally known method using chromatography or the like.

Next, a method for preventing infection according to the present invention is a method for preventing bacterial infection, including administering the above-described EGCG derivative or the antibacterial agent of the present invention to a subject. In the present invention, prevention of bacterial infection includes, for example, inhibition of bacterial infection, reduction of infection, and reduction and removal of infecting bacteria. Furthermore, a treatment method according to the present invention is a method for treating a disease caused by bacterial infection, including administering the above-described EGCG derivative or the antibacterial agent of the present invention to a subject. The present invention is characterized in that the EGCG derivative or the antibacterial agent of the present invention is used, and other configurations, conditions, etc. are by no means limited. The EGCG derivative, the antibacterial agent, the use method thereof, etc. are the same as described above, for example.

In the present invention, the subject is by no means limited, and examples thereof include humans and nonhuman animals. Examples of the nonhuman animals include: nonhuman mammals such as pigs, ferrets, rats, mice, and cows; and birds such as ducks and chickens. Furthermore, the subject may be a living organism itself or may be a cell or a tissue collected from a living organism, or a culture thereof, for example.

When the subject is a living organism, the administration method is not particularly limited, and examples thereof include parenteral administration and oral administration. Examples of the parenteral administration include transdermal administration, intraperitoneal administration, intravenous administration, intramuscular administration, subcutaneous administration, and rectal administration. Among them, transdermal administration is preferable. The administration method is as described above. Furthermore, conditions such as the form of the EGCG derivative and the antibacterial agent in the administration are as described above.

Furthermore, when the subject is a cell, a tissue, or the like collected from a living organism, the administration method, for example, is not particularly limited, and can be addition to a medium or the like, for example.

The timing of administrating the EGCG derivative or the antibacterial agent of the present invention to the subject is not particularly limited, and may be either before or after bacterial infection, for example.

The present invention provides an EGCG derivative for use in treatment of diseases caused by bacterial infection, and the EGCG derivative is as described above. The present invention also provides a composition containing an EGCG derivative for use in treatment of diseases caused by bacterial infection, and the EGCG derivative is as described above. The composition may contain one kind of the EGCG derivative, or two or more kinds of the EGCG derivatives, for example. When the composition contains two or more kinds of the EGCG derivatives, the combination of the kinds of the EGCG derivatives is not particularly limited. Examples of the combination include those described above with regard to the antibacterial agent.

EXAMPLES

Next, the present invention will be described with reference to examples. It is to be noted, however, that the present invention is by no means limited by the following examples.

Example 1

(1) Preparation of EGCG Derivatives

EGCG derivatives were prepared in the following manner.

1 g of EGCG, 927 mg of each type of acyl group donors shown in Table 1 below, and 50,000 U of lipase (trade name "Lipase PL", Meito Sangyo Co., Ltd.) were mixed with 100 ml of DMF. The resultant mixture was incubated at 57° C. for 2 hours to cause an enzyme reaction.

TABLE 1

| | | | Acyl group | |
| --- | --- | --- | --- | --- |
| | Acyl group donor | Acyl group | Carbon number | Main chain length |
| No. 1 | vinyl octanoate | octanoyl | C8 | 8 |
| No. 2 | vinyl laurate | lauroyl | C12 | 12 |
| No. 3 | vinyl palmitate | palmitoyl | C16 | 16 |
| No. 4 | vinyl stearate | stearoyl | C18 | 18 |
| No. 5 | vinyl eicosanoate | eicosanoyl | C20 | 20 |

Then, the reaction solution having undergone the incubation was filtered, and the filtrate obtained was concentrated. Thereafter, it was subjected to column chromatography (spherical, neutral, 40-50 μm, trade name "Silica gel N60", KANTO CHEMICAL CO., INC.) to remove unreacted acyl group donors as impurities. The thus-obtained reaction product was subjected to electrospray ionization mass spectrometry (ESI-MS). As a result, an EGCG derivative in which one acyl group shown in Table 1 was introduced to EGCG via an ester bond was obtained. Specifically, in $R^1$ or $R^2$ in the B ring or $R^5$ or $R^6$ in the D ring of the EGCG, one acyl group shown in Table 1 was introduced.

Furthermore, in order to identify which position of the EGCG was esterified, the reaction product was analyzed by proton nuclear magnetic resonance ($H^1$ NMR). The result thereof is shown in Table 2 below.

TABLE 2

|  | Acyl group | B ring | | D ring | | B/D* |
|---|---|---|---|---|---|---|
|  |  | $R^1$ | $R^2$ | $R^5$ | $R^6$ |  |
|  |  | Position | | | | |
|  |  | 3 | 4 | 4 | 5 |  |
| No. 1 | C8 octanoyl | 35: | 39: | 6: | 20 | 74/26 |
| No. 2 | C12 lauroyl | 30: | 39: | 9: | 22 | 69/31 |
| No. 3 | C16 palmitoyl | 38: | 35: | 7: | 20 | 73/27 |
| No. 4 | C18 stearoyl | 38: | 35: | 7: | 20 | 73/27 |
| No. 5 | C20 eicosanoyl | 38: | 36: | 8: | 19 | 73/27 |

*Ratio between B ring-esterified EGCG derivative and D ring-esterified EGCG derivative The EGCG derivatives in which the acyl groups Nos. 1 to 5 respectively were introduced are referred to as follows.

No. 1 EGCG-C8 or EGCG-octanonate
No. 2 EGCG-C12 or EGCG-laurate
No. 3 EGCG-C16 or EGCG-palmitate
No. 4 EGCG-C18 or EGCG-stearate
No. 5 EGCG-C20 or EGCG-eicosanoate These EGCG derivatives correspond to the EGCG derivatives represented by the chemical formula (2). In these EGCG derivatives, any one of $R^1$, $R^2$, $R^5$, and $R^6$ is the acyl group shown in Table 2, and other Rs are hydrogen atoms. These EGCG derivatives were used as antibacterial agents of Example 1.

(2) Antibacterial Effect

Methicillin-susceptible *Staphylococcus aureus* (MSSA) NCTC8325 and methicillin-resistant *Staphylococcus aureus* (MRSA) ATCC43300 were used as bacteria. The bacteria of each type were cultured using Mueller-Hinton Broth (MH-broth, Difco) as a medium. Then, the minimum inhibitory concentration (MIC) of each of the EGCG derivatives was measured by a broth microdilution method in accordance with the Clinical and Laboratory Standards Institute (CLSI) guidelines (hereinafter the same).

First, each of the EGCG derivatives was dissolved in 100% dimethyl sulfoxide (DMSO, Wako Pure Chemical Industries, Ltd.) so that the concentration thereof became 5120 µg/ml. The resultant solution was diluted with DMSO or sterile distilled water so as to prepare two-fold dilution series of antibacterial agent solutions. Specifically, up to a concentration of 1280 µg/ml, the dilution was performed using DMSO, and for concentrations lower than 1280 µg/ml, the dilution was performed using sterile distilled water. Each of these antibacterial agent solutions was dispensed to wells of a 96-well plate. The concentration of the EGCG derivative in the antibacterial agent solution dispensed to the wells was set to be 10 times as high as the final concentration. On the other hand, the bacteria were cultured in the MH-broth at 37° C. overnight, and the thus-obtained pre-culture solution was diluted with a new MH-broth so that the concentration thereof in the MH-broth became $10^{-4}$ ($10^4$-fold dilution), thus preparing a bacterial culture solution of about $1 \times 10^5$ CFU/ml (CFU: Colony Forming Unit, the number of viable cells). The bacterial culture solution was further added to each well, and the mixture was cultured at 37° C. for 18 hours. The ratio (volume ratio) between the antibacterial agent solution and the bacterial culture solution added to each well was set to 1:9 (the antibacterial agent solution: the bacterial culture solution), and the volume of the mixture of them per well was set to 100 µl in total. The final concentration of the EGCG derivative in the mixture was set to 8 µg/ml to 512 µg/ml, and the number of viable cells in the mixture was set to about $1 \times 10^5$ CFU/ml. Then, after the completion of the culture, the MIC was determined. Also, the turbidity ($OD_{600\ nm}$) was measured using a plate reader so as to identify minor differences.

As Comparative Example 1, the same procedures as in Example 1 were performed, except that unsubstituted EGCG was used as an antibacterial agent instead of the EGCG derivatives of Example 1. Furthermore, as a control, the same procedures as in Example 1 were performed, except that sterile distilled water, 100% DMSO, or 50% DMSO was used instead of the antibacterial agent solutions containing the EGCG derivatives.

The results of the MIC determination are shown in Table 3 below. Also, the results of the turbidity measurement regarding the MRSA are shown in FIG. 1. In the graph of FIG. 1, the vertical axis indicates the turbidity ($OD_{600\ nm}$), and the horizontal axis indicates the concentration (µg/ml) of EGCG or each EGCG derivative in the mixture. In the graph of FIG. 1, an open rhombus (◇) indicates the results regarding EGCG-C8, an open square (□) indicates the results regarding EGCG-C12, an open circle (○) indicates the results regarding EGCG-C16, an open triangle (△) indicates the results regarding EGCG-C18, a filled circle (●) indicates the results regarding EGCG-C20, and x indicates the results regarding EGCG.

TABLE 3

| Bacterial Strain | MIC (µg/ml) | | | | | |
|---|---|---|---|---|---|---|
|  | C8 | C12 | C16 | C18 | C20 | EGCG |
| MSSA | 8 | 8 | 8 | 16 | — | 128 |
| MRSA | — | 16 | 8 | 32 | 128 | 256 |

As can be seen from FIG. 1 and Table 3, the EGCG derivatives of Example 1 could inhibit the propagation of the MSSA and MRSA more effectively than EGCG of Comparative Example 1. In particular, EGCG-C12 and EGCG-C16 exhibited a remarkable propagation-inhibiting effect against the MRSA.

(3) Bactericidal Effect

The bactericidal effect of EGCG-C16 against MRSA ATCC43300, *E. coli* MG1655, and *P. aeruginosa* PAO1 was measured. Each strain of bacteria was cultured using an MH-broth as a medium.

The antibacterial agent solution and the bacterial culture solution were mixed together and the resultant mixture was cultured at 37° C. in the same manner as described in the above section (2), except that the final concentration of the EGCG-C16 in the mixture were set to: 6.25 µg/ml or 25 µg/ml for the MRSA; 200 µg/ml for the *E. coli*; and 50 µg/ml, 100 µg/ml, and 200 µg/ml for the *P. aeruginosa*. The number of viable cells in the mixture of the antibacterial agent solution and the bacterial culture solution was set to 1×10⁵ CFU/ml. Then, after a lapse of a predetermined time from the start of the culture (0 hours, 2 hours, 4 hours, and 6 hours), the culture solution was collected and diluted with physiological saline so as to prepare 10-fold dilution series of solutions. 100 μl of each of the diluted bacterial culture solutions was placed on a petri dish. The diluted bacterial culture solution was hardened by mixing it with 10 ml of a Trypticase-soy Agar (BBL) that was kept at 50° C., and cultured at 37° C. overnight. Then, the number of the formed colonies (CFU/ml) was counted, and the number of remaining viable cells was measured.

Figure 2:
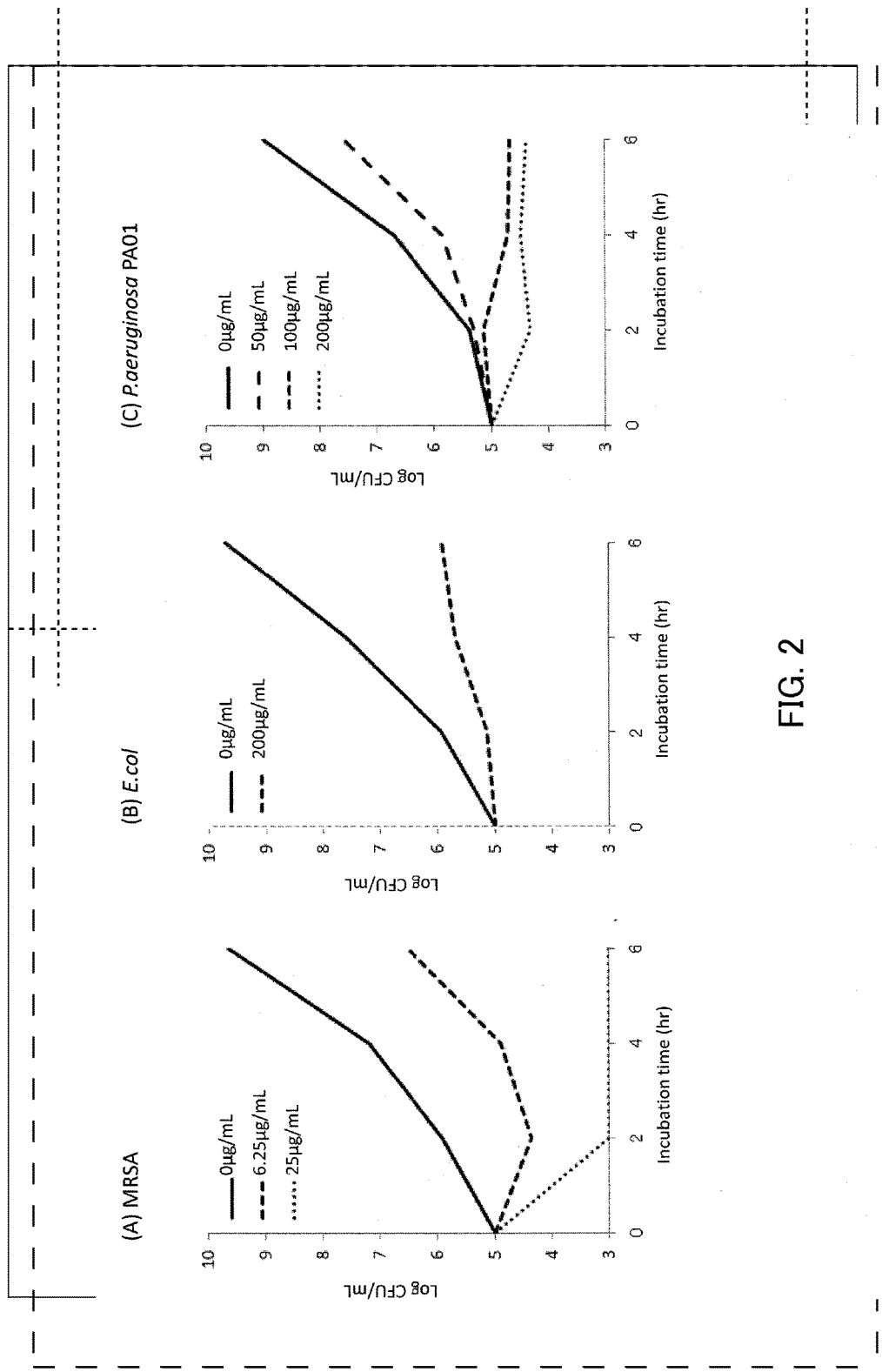
FIG. 2 show graphs each showing the antibacterial effect of an EGCG derivative in Example 1 of the present invention.

The results thereof are shown in FIG. 2. FIGS. 2(A) to 2(C) are graphs each representing the change in the number of remaining viable cells with time by logarithm. FIG. 2(A) shows the results obtained regarding the MRSA ATCC43300; FIG. 2(B) shows the results obtained regarding the *E. coli* MG1655; and FIG. 2(C) shows the results obtained regarding the *P. aeruginosa* PAO1. In FIGS. 2(A) to 2(C), the x axis indicates a treatment time (hour), and the y axis indicates the logarithm of the number of colonies (CFU/ml). The number of colonies at the treatment time of 0 hours was 1×10⁵ CFU/ml. Furthermore, in FIGS. 2(A) to 2(C), 0 μg/ml indicates the result of measuring the number of remaining viable cells when the incubation was carried out without adding the EGCG derivative.

As can be seen from FIG. 2(A), when the concentration of EGCG-C16 was 25 μg/ml, EGCG-C16 not only inhibited the propagation but also reduced the number of viable cells. This demonstrates that EGCG-C16 exhibits a remarkable bactericidal action against the MRSA. Furthermore, as can be seen from FIGS. 2(B) and 2(C), EGCG-C16 exhibited a bacteriostatic action of inhibiting the propagation (propagation inhibiting action) against the *E. coli* MG1655 and the *P. aeruginosa* PAO1.

Example 2

(1) Preparation of EGCG Derivatives

EGCG derivatives were prepared in the following manner.

EGCG derivatives were prepared in the same manner as in Example 1, except that acyl group donors shown in Table 4 below were used.

TABLE 4

| | Acyl group donor | Acyl group | Carbon number | Main chain length |
|---|---|---|---|---|
| No. 6 | vinyl palmitate | palmitoyl | C16 | 16 |
| No. 7 | vinyl octanoate | octanoyl | C8 | 8 |
| No. 8 | vinyl stearate | stearoyl | C18 | 18 |
| No. 9 | vinyl oleate | oleoyl (ene) | C18E | 18 |
| No. 10 | vinyl linoleate | linoleyl (diene) | C18DE | 18 |
| No. 11 | α-vinyl linolenate | linolenyl (triene) | C18TE | 18 |
| No. 12 | vinyl palmitoleate | palmitoleyl (ene) | C16E | 16 |

Furthermore, in order to identify which position of EGCG was esterified, the reaction product was analyzed by proton nuclear magnetic resonance (H¹ NMR). The results thereof are shown in Table 5 below.

TABLE 5

| | | B ring | | D ring | | |
|---|---|---|---|---|---|---|
| | | R¹ | R² | R⁵ | R⁶ | |
| | | Position | | | | |
| | Acyl group | 3 | 4 | 4 | 5 | B/D* |
| No. 6 | C16 palmitoyl | 38: | 35: | 7: | 20 | 73/27 |
| No. 7 | C8 octanoyl | 35: | 39: | 6: | 20 | 74/26 |
| No. 8 | C18 stearoyl | 38: | 35: | 7: | 20 | 73/27 |
| No. 9 | C18E oleoyl | 41: | 34: | 5: | 20 | 75/25 |
| No. 10 | C18DE linoleyl | 28: | 26: | 5: | 45 | 50/50 |
| No. 11 | C18-TE linolenyl | 15: | 19: | 4: | 62 | 34/66 |
| No. 12 | C16E palmitoleyl | 28: | 37: | 9: | 26 | 65/35 |

*Ratio between B ring-esterified EGCG derivative and D ring-esterified EGCG derivative The EGCG derivatives in which the acyl groups No. 6 to No. 12 respectively were introduced are referred to as follows.

No. 6 EGCG-C16 or EGCG-palmitate

No. 7 EGCG-C8×2 or EGCG-dioctanoate

No. 8 EGCG-C18 or EGCG-stearate

No. 9 EGCG-C18E or EGCG-oleate

No. 10 EGCG-C18DE or EGCG-linolate

No. 11 EGCG-C18TE or EGCG-α-linoleate

No. 12 EGCG-C16E or EGCG-palmitoleate

These EGCG derivatives correspond to the EGCG derivatives represented by the chemical formula (2). In these EGCG derivatives, any one of R¹, R², R⁵, and R⁶ is the acyl group shown in Table 5, and other Rs are hydrogen atoms. These EGCG derivatives were used as antibacterial agents of Example 2.

(2) Antibacterial Effect

Each of the EGCG derivatives was dissolved in 100% DMSO so that the concentration thereof became 1280 μg/ml. The thus-obtained solutions were diluted with sterile distilled water, thus preparing antibacterial agent solutions. Then, regarding each antibacterial agent solution, the minimum inhibitory concentration (MIC) was measured in the same manner as described in Section (2) of Example 1, except that MSSA NCTC8325, MSSA ATCC25923, MSSA ATCC12600, MSSA ATCC29213, five MSSA clinical isolates (Nos. 1 to 5), and MRSA ATCC43300 and seven MRSA clinical isolates (Nos. 6 to 12) were used as bacteria. The results thereof are shown in Table 6 below.

As Comparative Example 2, the same procedures as in Example 2 were performed, except that unsubstituted EGCG was used as an antibacterial agent instead of the EGCG derivatives of Example 2. Furthermore, as a control, the same procedures as in Example 2 were performed, except that sterile distilled water was used instead of the antibacterial agent solutions containing the EGCG derivatives.

TABLE 6

| | MIC (μg/mL) | | | | | | | |
|---|---|---|---|---|---|---|---|---|
| | Ex. 2 | | | | | | | Comp. Ex. 2 |
| Strain | C8 × 2 | C16 | C16E | C18 | C18E | C18DE | C18TE | EGCG |
| (MSSA) | | | | | | | | |
| S. aureus NCTC8325 | 4 | 8 | 16 | 16 | 16 | 16 | 4 | 128 |
| MSSA ATCC25923 | 16 | 16 | 32 | 32 | 32 | 32 | 32 | >128 |
| MSSA ATCC12600 | 8 | 16 | 16 | 32 | 32 | 16 | 16 | >128 |
| MSSA ATCC29213 | 16 | 16 | 16 | 32 | 32 | 16 | 16 | >128 |
| No. 1 | 16 | 16 | 16 | 32 | 32 | 16 | 16 | >128 |
| No. 2 | 16 | 16 | 16 | 32 | 32 | 16 | 16 | >128 |
| No. 3 | 16 | 16 | 16 | 32 | 32 | 16 | 16 | >128 |
| No. 4 | 16 | 16 | 16 | 32 | 32 | 16 | 16 | >128 |
| No. 5 | 16 | 16 | 16 | 32 | 32 | 16 | 16 | 128 |
| (MRSA) | | | | | | | | |
| MRSA ATCC43300 | 16 | 16 | 16 | 32 | 32 | 16 | 16 | >128 |
| No. 6 | 16 | 16 | 16 | 32 | 32 | 32 | 16 | >128 |
| No. 7 | 16 | 16 | 16 | 32 | 16 | 16 | 16 | >128 |
| No. 8 | 4 | 8 | 8 | 16 | 8 | 8 | 8 | 128 |
| No. 9 | 16 | 32 | 64 | | 64 | 64 | 64 | >128 |
| No. 10 | 16 | 16 | 16 | 32 | 16 | 16 | 16 | >128 |
| No. 11 | 32 | 32 | 64 | 64 | 64 | 32 | 64 | >128 |
| No. 12 | 16 | 16 | 16 | 64 | 32 | 16 | 16 | >128 |

As can be seen from Table 6, the EGCG derivatives of Example 2 exhibited better antibacterial properties than EGCG of Comparative Example 2 against the MSSA and MRSA. Furthermore, as described below, it was found that, comparing the EGCG derivatives having the same number of carbon atoms in their acyl groups, the EGCG derivative in which an unsaturated fatty acid having two or more unsaturated bonds was introduced exhibited a higher antibacterial effect than the EGCG derivative in which a saturated fatty acid was introduced. It was also found that the EGCG derivative in which a saturated fatty acid having 16 carbon atoms was introduced and the EGCG derivative in which two molecules of saturated fatty acid having 8 carbon atoms was introduced exhibited similar antibacterial effects, and they both exhibited high water solubility and chemical structure stability.

EGCG-C16≤EGCG-C16E
EGCG-C18≤EGCG-C18E<EGCG-C18DE≤EGCG-C18TE
EGCG-C16≤EGCG-C8×2

(3) Antibacterial Spectrum (MIC)

Regarding the respective type strains shown in Tables 7 and 8 below, the MIC measurement was performed using the antibacterial agent solutions of Example 2 in the same manner as described in Section (2) of Example 1, except for the following. The antibacterial agent solutions were prepared by dissolving the EGCG derivatives of Example 2 in 100% DMSO and then diluting the resultant mixtures with sterile distilled water. The respective strains were derived from ATCC or NCTC. As Moraxella catarrhalis and Aspergillus fumigatus, clinical isolates thereof without an acquired resistance mechanism were used. For nutrient-rich bacteria, namely, Streptococcus pneumoniae ATCC49619, Streptococcus pyogenes ATCC19615, Streptococcus agalactiae ATCC13813, Moraxella catarrhalis, and Haemophilis influenzae ATCC49766, Strepto Haemo supplement (Eiken Chemical Co., Ltd.) was added to media for culturing them. The MIC measurement with respect to fungi was carried out by a broth microdilution method using a RPMI1640/MOPS (pH 7.0) medium in accordance with CLSI guidelines. About 2×10³ cells/ml of fungi were inoculated to the medium. After the culture at 35° C. for 24 to 48 hours, the MIC was determined. Also, regarding the antibacterial agent solution of Comparative Example 2, the MIC was measured in the same manner.

The results of determining the MIC of each derivative against the respective type strains are shown in Tables 7 and 8. Table 7 shows the results obtained regarding the bacteria, and Table 8 shows the results obtained regarding the fungi.

TABLE 7

| | MIC (μg/mL) | | | | | | | |
|---|---|---|---|---|---|---|---|---|
| | Ex. 2 | | | | | | | Comp. Ex. 2 |
| Strain | C8 × 2 | C16 | C16E | C18 | C18E | C18DE | C18TE | EGCG |
| Bacillus subtilus ATCC6051 | 32 | 16 | 16 | 32 | 32 | 32 | 32 | 64 |
| Bacillus cereus ATCC14579 | 16 | 16 | 16 | 32 | 32 | 16 | 32 | 64 |
| Staphylococcus aureus NCTC8325 | 16 | 16 | 16 | 32 | 32 | 16 | 16 | 128 |
| Staphylococcus aureus ATCC43300 (MRSA) | 64 | 32 | 64 | 32 | 64 | 64 | 64 | 128 |
| Staphylococcus epidermis ATCC14990 | 64 | 32 | 64 | 32 | 64 | 64 | 64 | 128 |
| Streptococcus pneumoniae ATCC49619 | 16 | 16 | 16 | | 16 | 16 | 16 | 32 |
| Streptococcus pyogenes ATCC19615 | 32 | 64 | 64 | 64 | 64 | 64 | 64 | 128 |
| Streptococcus agalactiae ATCC13813 | 64 | >64 | >64 | 64 | >64 | >64 | >64 | 256 |
| Enterococcus faecalis ATCC29212 | 64 | 16 | 64 | 32 | >64 | 64 | 64 | 256 |
| Micrococcus lutus ATCC9341 | 64 | 64 | 64 | 64 | 64 | 64 | 64 | 128 |

TABLE 7-continued

| | MIC (μg/mL) | | | | | | | |
|---|---|---|---|---|---|---|---|---|
| | Ex. 2 | | | | | | | Comp. Ex. 2 |
| Strain | C8 × 2 | C16 | C16E | C18 | C18E | C18DE | C18TE | EGCG |
| Neisseria meningitidis | 16 | 16 | 16 | 16 | 16 | 16 | 16 | 32 |
| Moraxella catarrhalis | 32 | 64 | 64 | 64 | 32 | 64 | 32 | 128 |
| Haemophilis influenzae ATCC49766 | 16 | 16 | 16 | | 16 | 16 | 16 | 32 |
| Neisseria gonorrhoeae ATCC49226 | 16 | 16 | 16 | 16 | 16 | 16 | 16 | 32 |
| Escherichia coli ATCC25922 | 64 | 64 | 64 | 64 | 64 | 64 | 64 | 128 |
| Klebsiella oxytoca ATCC8724 | 64 | 64 | 64 | 64 | 64 | 64 | 64 | 128 |
| Enterobacter cloacae ATCC13047 | 64 | 64 | 64 | 64 | 64 | 64 | 64 | 128 |
| Enterobacter aerogenes ATCC13048 | 16 | 32 | 32 | 32 | 32 | 32 | 32 | 64 |
| Proteus vulgaris ATCC13315 | | | | | | 32 | | 64 |
| Serratia marcescens ATCC13880 | 64 | 64 | 64 | 64 | 64 | 64 | 64 | 128 |
| Yersinia enterocolitica ATCC9610 | 32 | 32 | 32 | 32 | 32 | 32 | 32 | 64 |
| Pseudomonas aeruginosa ATCC7700 | | | | 32 | | | | 64 |
| Stenotrophomonas maltophilia ATCC13637 | 32 | 32 | 32 | 32 | 32 | 32 | 32 | 64 |

TABLE 8

| | MIC (μg/mL) | | | | | | | |
|---|---|---|---|---|---|---|---|---|
| | Ex. 2 | | | | | | | Comp. Ex. 2 |
| Strain | C8 × 2 | C16 | C16E | C18 | C18E | C18DE | C18TE | EGCG |
| Candida albicans ATCC24433 | 32 | 32 | 16 | 16 | 16 | 16 | 16 | 64 |
| Candida parapsilosis ATCC22019 | 16 | 16 | 16 | 16 | 16 | 16 | 16 | 64 |
| Candida tropicalis ATCC750 | 32 | 32 | 16 | 32 | 32 | 32 | 16 | 64 |
| Candida krusei ATCC6258 | 16 | 16 | 16 | 16 | 16 | 16 | 16 | 64 |
| Candida glabrata ATCC90030 | 16 | 16 | 16 | 16 | 16 | | | 32 |
| Cryptococcus neoformans ATCC90112 | 16 | 8 | 8 | 16 | 16 | 8 | 8 | 64 |
| Aspergillus fumigatus | 32 | 32 | 16 | 32 | 32 | 32 | 16 | 64 |

As can be seen from Tables 7 and 8, each of the EGCG derivatives of Example 2 exhibited an antibacterial activity against all the strains. As can be seen from Table 7, each of the EGCG derivatives exhibited a higher antibacterial effect than EGCG against the Gram-positive bacteria. Also, as can be seen from Table 7, each of the EGCG derivatives exhibited a high antibacterial activity particularly against the staphylococci, and EGCG-C16 and EGCG-C18 exhibited the strongest antibacterial effect against *Staphylococcus epidermids* ATCC14990 (*S. epidermidis*). Furthermore, as can be seen from Table 8, each of the EGCG derivatives exhibited an antibacterial activity also against the respective types of fungi. In particular, EGCG-C16E and EGCG-C18TE exhibited the highest antifungal effect. The antifungal effect of EGCG-C16E was 2 to 8 times higher than that of the EGCG of Comparative Example 2.

Example 3

Regarding EGCG-C16, whether or not the antibacterial action thereof against MSSA and MRSA is inhibited by the addition of: peptidoglycan (PG) or D-Ala-D-Ala, which are each a cell wall component; or lipopolysaccharide (LPS), which is an outer membrane component, was examined. The MIC measurement was carried out in the manner described in Section (2) of Example 2.

In Example 3, EGCG-C16 prepared in Example 1 was used as an antibacterial agent. In Comparative Example 3, unsubstituted EGCG was used as an antibacterial agent. In a reference example, vancomycin (VCM, SIGMA) and teicoplanin (TEIC, SIGMA) that bind to PG or D-Ala-D-Ala directly and ampicillin (ABPC, SIGMA) that inhibits PG synthase were used as antibacterial agents. Antibacterial agent solutions of EGCG-C16 and EGCG were prepared in the same manner as described in Section (2) of Example 1. Antibacterial agent solutions of the antibacterial agents other than EGCG-C16 and EGCG were prepared by dissolving them in PBS.

As additives, PG (Peptidoglycan *Staphylococcus aureus*, SIGMA-ALDRICH), D-Ala-D-Ala (SIGMA-ALDRICH), and LPS (Lipopolysaccharide *Salmonella*, SIGMA-ALDRICH) were provided. Each of the additives was dissolved in PBS, and the resultant solution was used as an additive solution.

Dilution series of the antibacterial agent solutions were prepared. Each of them was dispensed to a 96-well plate. Further, the additive solution was added thereto and mixed. After that, a bacterial culture solution of MRSA ATCC43300 or MSSA ATCC25923 was added thereto and cultured at 37° C. for 18 hours. In the mixture of the antibacterial agent solution, the additive solution, and the bacterial culture solution, the final concentrations of PG, D-Ala-D-Ala, and LPS were each set to 30 μg/ml. Unless otherwise stated, the minimum inhibitory concentration (MIC) was calculated in the same manner as described in Section (2) of Example 2. The results thereof are shown in Table 9 below.

TABLE 9

| | MSSA (ATCC25923) | | | MRSA (ATCC43300) | | |
|---|---|---|---|---|---|---|
| | MH-broth | +PG (30 μg/mL) | +LPS (30 μg/mL) | MH-broth | +PG (30 μg/mL) | +LPS (30 μg/mL) |
| EGCG-C16 | 16 | 32 | 16 | 16 | 32 | 16 |
| EGCG | >64 | >64 | >64 | >64 | >64 | >64 |
| VCM | 2 | 4 | 2 | 2 | 4 | 2 |
| TEIC | 1 | 2 | 1 | 0.5 | 1 | 1 |
| ABPC | 0.25 | 0.125 | 0.25 | 32 | 32 | 32 |

| | MSSA (ATCC25923) | | | MRSA (ATCC43300) | | |
|---|---|---|---|---|---|---|
| | MH-broth | +PG (30 μg/mL) | +D-Ala-D-Ala (30 μg/mL) | MH-broth | +PG (30 μg/mL) | +D-Ala-D-Ala (30 μg/mL) |
| EGCG-C16 | 16 | 32 | 16 | 8 | 16 | 8 |
| VCM | 1 | 2 | 16 | 1 | 2 | 16 |
| TEIC | 1 | 2 | 32 | 0.5 | 1 | 16 |
| ABPC | 0.25 | 0.25 | 0.25 | 16 | 8 | 16 |

MH-broth: medium free of the above additives

As can be seen from Table 9, EGCG of Comparative Example 3 exhibited a weak antibacterial activity, and no change in MIC was observed. The MIC of the EGCG derivative of Example 3 was doubled by the addition of PG, similarly to the MIC of VCM and TEIC. From this, it is considered that the EGCG derivative of Example 3 binds or adsorbs to the cell wall component PG directly, similarly to VCM and TEIC. It is speculated that this contributes to the antibacterial activity of the EGCG derivative. Furthermore, the MIC of VCM and TEIC increased to 16 times or more by adding D-Ala-D-Ala, whereas D-Ala-D-Ala gave no influence on the EGCG derivative. This revealed that the binding site for the EGCG derivative in PG is not D-Ala-D-Ala, unlike the cases of VCM and TEIC.

Example 4

The damaging properties of EGCG-C16 on membrane structures of MSSA and MRSA were examined.

As an antibacterial agent, the EGCG-C16 prepared in Example 1 was used in Example 4; EGCG was used in Comparative Example 4; and membrane-damaging peptide NISIN (MP Biomedicals) was used in a reference example. Antibacterial agent solutions of EGCG-C16 and EGCG were prepared by dissolving them in DMSO so as to achieve top concentrations, respectively. An antibacterial agent solution of the other antibacterial agent was prepared by dissolving it in PBS and diluted with PBS as appropriate. The influence of DMSO used for dissolving the antibacterial agents also was considered.

MSSA ATCC25923 and MRSA ATCC43300 were subjected to shaking culture in MH-broths (Difco) until they reached a late stage in the exponential growth phase. The thus-obtained culture solutions were each centrifuged at 7000 rpm for 10 minutes, and bacterial cells that had settled were suspended in PBS. The suspension of the bacterial cells was added to wells of a 384 black plate, and each of the antibacterial agent solutions was further added thereto and mixed. The resultant mixture was incubated at 37° C. for 15 minutes. Subsequently, a dead cell-staining dye (trade name "SYTOX Green", LONZA) was mixed in each well so that the concentration thereof became 10 μmol/l, and the resultant mixture was incubated at 37° C. for 10 minutes. The final concentrations of the respective antibacterial agents were as follows: 4, 8, 16, and 32 μg/ml for the EGCG derivative; 8, 16, 32, 64, and 128 μg/ml for EGCG; and 1, 2, 4, and 8 μg/ml for NISIN. Then, after the incubation, each well of the plate was irradiated with excitation light of 488 nm, and the fluorescence at 530 nm was measured using a Microplate Reader SH-8100 (trade name, CORONA ELECTRIC Co., Ltd.). On the other hand, as a control, the fluorescence intensity was measured in the same manner, except that PBS or 10% DMSO was added instead of the antibacterial agent solutions. Then, regarding each of the MSSA and MRSA, the ratio of the fluorescence intensity when each of the agents was added was calculated assuming that the fluorescence intensity obtained in the control (PBS) was 1. The SYTOX Green is a DNA intercalator that does not penetrate membranes of living cells. As this fluorescence intensity becomes relatively high, it means that membrane damaging properties of the agent are relatively high, so that the intercalator is incorporated into bacterial cells more easily. Thus, the ratio of the fluorescence intensity greater than 1 indicates that the agent has a strong membrane-damaging action, whereas the ratio much smaller than 1 suggests the possibility that the permeability action on the bacterial membrane might be reduced.

Figure 3:
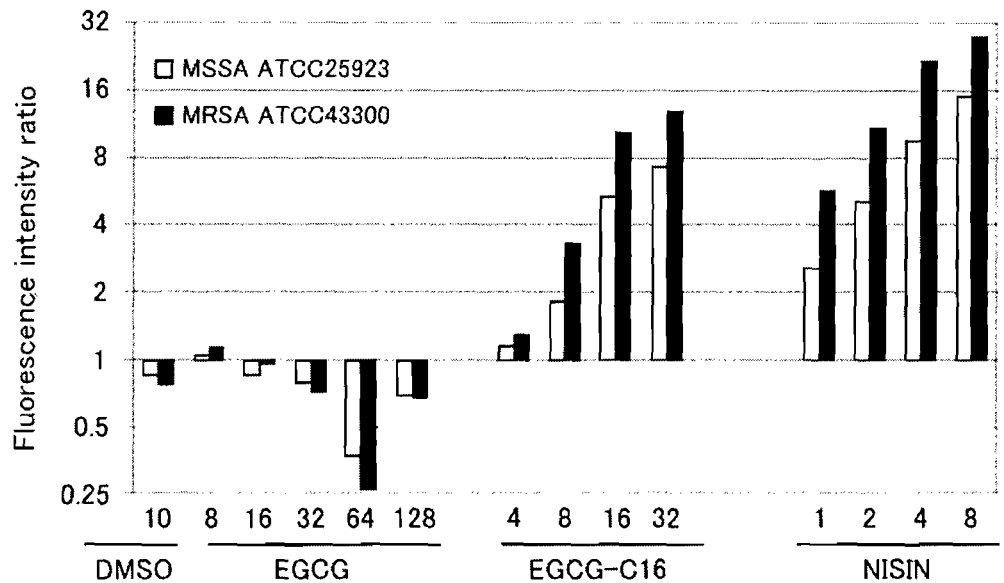
FIG. 3 is a graph showing cell membrane-damaging properties of an EGCG derivative in Example 4 of the present invention.

The results thereof are shown in FIG. 3. FIG. 3 is a graph representing the membrane damaging properties of each antibacterial agent to the MSSA and MRSA by the fluorescence intensity of the SYTOX Green. In FIG. 3, the y axis indicates the fluorescence intensity ratio assuming that the fluorescence intensity in the control was 1. In FIG. 3, the numbers shown above the respective antibacterial agents indicate the concentrations. At each concentration of the antibacterial agents, the left (white) bar indicates the result obtained regarding the MSSA ATCC25923, and the right (black) bar indicates the result obtained regarding the MRSA ATCC43300. As can be seen from FIG. 3, EGCG of Comparative Example 4 exhibited the fluorescence intensity ratio smaller than 1. From this, it is speculated that EGCG of Comparative Example 4 has weak cell membrane-damaging properties, so that the introduction of the intercalator into the bacterial cells was inhibited still more strongly than in the control (PBS), owing to physical adsorption on the cell walls. A similar tendency was observed in the 10% DMSO, although such a tendency was slight. In contrast, EGCG-C16 of Example 4 exhibited a very high fluorescence intensity ratio, similarly to the membrane-damaging peptide NISIN of the reference example. Thus, it is speculated that EGCG-C16 of Example 4 obviously has a cell membrane-damaging properties. Furthermore, there was observed a tendency for this action of EGCG-C16 to become weak at a high concentration of 64 µg/ml. From this, it is speculated that EGCG-C16 also has a similar action to EGCG. From the results described above, it is speculated that the EGCG derivative could exhibit a higher antibacterial activity than EGCG, because not only it was bound to cell walls as described above but also it exhibited a membrane-damaging action.

Example 5

Regarding EGCG derivatives, the influence of the multidrug efflux pump on their antibacterial activities against *Escherichia coli* MG1655 was examined.
(1) EGCG Derivatives
As EGCG derivatives, EGCG-C16, EGCG-C8×2, EGCG-C16E, and EGCG-C18TE of Example 2 were used.
(2) Antibacterial Effect
Using the EGCG derivatives, the minimum inhibitory concentration (MIC) was measured in the same manner as described in Section (2) of Example 2, except that *Escherichia coli* MG1655 (hereinafter referred to as a wild-type strain) and gene deletion strains of *Escherichia coli* MG1655 were used as the bacteria. The gene deletion strains were: strains obtained by deleting the efflux pump genes, namely, acrB, acrD, and acrEF, respectively, in *Escherichia coli* MG1655 (ΔacrD, ΔacrEF, and ΔacrB); and a strain obtained by deleting the outer membrane protein tolC gene that couples to proteins encoded by the efflux pump genes (ΔtolC).

As Comparative Example 5, the minimum inhibitory concentration (MIC) was measured in the same manner as in Example 5, except that EGCG was used instead of the EGCG derivative. The results thereof are shown in Table 10 below.

TABLE 10

| | Antibacterial agent | MIC (µg/ml) | | | | |
| --- | --- | --- | --- | --- | --- | --- |
| | | MG1655 (wild type) | ΔacrD | ΔacrEF | ΔacrB | ΔtolC |
| Ex. 5 | EGCG-C8 × 2 | >128 | >128 | >128 | 64 | 32 |
| | EGCG-C16 | >128 | >128 | >128 | 64 | 64 |
| | EGCG-C16E | >128 | >128 | >128 | 64 | 64 |
| | EGCG-C18TE | >128 | >128 | >128 | 64 | 64 |
| Comp. Ex. 5 | EGCG | >256 | >256 | >256 | 128 | 128 |

As can be seen from Table 10, the EGCG derivatives exhibited higher antibacterial activities against ΔacrB and ΔtolC than against the wild-type strain, and their antibacterial activities were twice as high as the antibacterial activity of EGCG. Furthermore, as can be seen from Table 10, the antibacterial properties of each of the EGCG derivatives and EGCG against the wild-type strain (MG1655) and against the gene deletion strains (ΔacrD, ΔacrEF) show no significant difference. In contrast, by the deletion of acrB, the EGCG derivative and EGCG exhibited excellent antibacterial properties against the gene deletion strain (ΔacrB). These antibacterial properties were almost comparable to the antibacterial properties against the gene deletion strain (ΔtolC) obtained by deleting the outer membrane protein gene tolC that couples to all the RND-type pumps. From this result, it is speculated that the EGCG derivatives and EGCG are pumped out mainly to the protein AcrB encoded by acrB.

Example 6

Regarding EGCG-C16, antibacterial properties thereof against staphylococci when used in combination with a β-lactam agent, namely, ampicillin (ABPC) or imipenem (IPM), were examined by the checker-board method.

EGCG-C16 was dissolved in 100% DMSO, and each of the above-described β-lactam agents was dissolved in sterile distilled water. Thereafter, they were diluted with sterile distilled water so as to achieve predetermined concentrations, and the respective agents at the respective concentrations were combined one another. The change in MIC of each β-lactam agent by the addition of EGCG-C16 was measured by the checker-board method. The final concentration of EGCG-C16 was set to 0, 2, 4, 8, 16, 32, 64, and 128 µg/ml; the final concentration of ABPC was set to 0, 1, 2, 4, 8, 16, 32, and 64 µg/ml; and the final concentration of IPM was set to 0, 0.001, 0.002, 0.004, 0.008, 0.016, and 0.031 µg/ml. The minimum inhibitory concentration (MIC) of each of the above-described β-lactam agents when used in combination with EGCG-C16 was measured in the same manner as described in Section (2) of Example 2, except that the MRSA ATCC43300 and the MRSA clinical isolate No. 8 used in Example 2 were used as the bacteria.

As Comparative Example 6, the minimum inhibitory concentration (MIC) was measured in the same manner as in Example 6, except that EGCG was used instead of EGCG-C16. The results thereof are shown in Table 11 below. Table 11 shows change in MIC of each β-lactam agent when used in combination with EGCG-C16 or EGCG at the predetermined concentrations.

TABLE 11

| Strain | Antibacterial agent | Concentration of EGCG-C16 or EGCG (µg/ml) | | | | | | | |
| --- | --- | --- | --- | --- | --- | --- | --- | --- | --- |
| | | 0 | 2 | 4 | 8 | 16 | 32 | 64 | 128 |
| Change in MIC of ABPC | | | | | | | | | |
| ATCC43300 | EGCG-C16 | 32 | 16 | 8 | 1 | *MIC | | | |
| ATCC43300 | EGCG | 32 | | | 8 | 4 | 4 | 2 | 1 |
| No. 8 | EGCG-C16 | 64 | 32 | 16 | 2 | *MIC | | | |
| No. 8 | EGCG | 64 | | | 4 | 8 | 8 | 4 | 1 |
| Change in MIC of IPM | | | | | | | | | |
| ATCC43300 | EGCG-C16 | 0.016 | 0.016 | 0.016 | 0.004 | *MIC | | | |
| ATCC43300 | EGCG | 0.016 | | | 0.016 | 0.031 | 0.031 | 0.031 | 0.016 |

*MIC: The minimum EGCG-C16 concentration when the growth of the bacteria was inhibited using EGCG-C16 alone under a β-lactam agent free condition.

As can be seen from Table 11, by using the EGCG derivative in combination, the MIC of each β-lactam agent against the ATCC43300 and the clinical isolate No. 8 could be reduced remarkably as compared to the case where EGCG was used in combination. This demonstrates that the EGCG derivative can remarkably improve the antibacterial properties of the β-lactam agents. Furthermore, EGCG exhibited a weak antagonistic action against the ATCC43300, which is IPM susceptible, when the concentration thereof was 16 to 64 μg/ml, whereas the EGCG derivative did not exhibit an antagonistic action in the examined concentration range.

Example 7

With regard to an EGCG derivative having an acyl group in the D ring and an EGCG derivative having an acyl group in the B ring, the metabolic stability was examined.

EGCG-C16 was prepared in the same manner as in Example 1. As EGCG-C16, a mixture of a derivative represented by the chemical formula (2) in which the 3-position ($R^1$) in the B ring is a palmitoyl group (C16) and a derivative represented by the chemical formula (2) in which the 4-position ($R^2$) in the B ring is a palmitoyl group (hereinafter, the mixture is referred to as a "B-ring derivative"), and a mixture of a derivative represented by the chemical formula (2) in which the 4-position ($R^5$) in the D ring is a palmitoyl group (C16) and a derivative represented by the chemical formula (2) in which the 5-position ($R^6$) in the D ring is a palmitoyl group (hereinafter, the mixture is referred to as a "D-ring derivative") were used. Note here that, in the chemical formula (2), Rs other than the above-described Rs are all hydrogen atoms.

1.25 μl of 10 mg/ml mouse microsome (Charles River Laboratories Japan, Inc.) and 0.25 μl of an aqueous solution of 1% 3-[(3-cholamidopropyl)dimethylammonio]-1-propanesulfonate (CHAPS, Dojindo) were dissolved in 8.5 μl of an aqueous solution of 0.1 mol/l potassium phosphate (pH 7.4). This mixed solution was incubated on ice for 30 minutes so as to elute a glucuronic acid metabolic enzyme in the microsome. This solution was used as a reaction solution A. Next, 10 μl of 10 mmol/l EGCG-C16, 5.0 μl of 10 mg/ml L-α-lysophosphatidylcholine (Wako), and 20 μl of 30 mmol/l UDP-glucuronic acid trisodium (UDP-Glc; Nacalai Tesque, Inc.) were dissolved in 155 μl of reaction buffers (1.0 mol/l Tris-HCl (pH 7.4):0.1 mol/l $MgCl_2$: $H_2O$=2:1:13), respectively. The resultant mixtures were used as reaction solutions B, respectively. Subsequently, in a hot-water bath at 37° C., the reaction solution A and each of the reaction solutions B were mixed, thereby causing a reaction for conjugating glucuronic acid of EGCG-C16. After allowing each mixture to react for predetermined times (0, 0.5, 1, 1.5, 3, 6, 12, and 24 minutes), 200 μl of acetonitrile (HPLC grade; KANTO CHEMICAL CO., INC.) was added per 200 μl of the reaction solution to terminate the metabolic reaction. Subsequently, the reaction solution was filtered through a 0.45 μm DISMIC filter made of PTFE (Ekicrodisc 13CR; Gelman Science), after which about 40 μl of the thus-obtained filtrate was subjected to HPLC analysis as a metabolic reaction solution under the following conditions.

Figure 4:
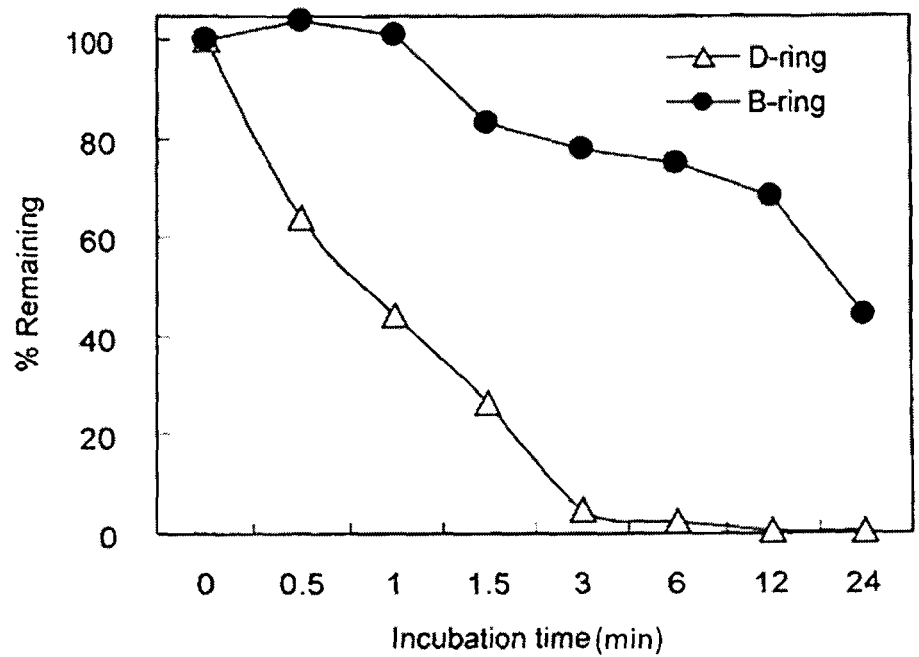
FIG. 4 is a graph showing the metabolic stability of EGCG derivatives in Example 7 of the present invention.

A WP300-C4 column (5 μm, 4.6×150 mm, GL Science) was mounted on a HPLC analysis system (JASCO Corporation), and each of the metabolic reaction solutions of EGCG-C16 was analyzed at a wavelength of 265 nm. For a mobile phase of the HPLC analysis, distilled water (HPLC grade; KANTO CHEMICAL CO., INC.) containing 0.1% trifluoro acetic acid (HPLC grade; Wako) was used as a solution A and acetonitrile (HPLC grade; KANTO CHEMICAL CO., INC.) containing 0.1% trifluoro acetic acid was used as a solution B. The percentage by volume of the solution B in the whole mobile phase (solution A+solution B) was set so as to provide gradient, specifically, set to 0%, 0%, 25%, 100%, 100%, 0%, and 0%, at an elution time of 0, 3, 10, 22, 26, 28, and 30 minutes, respectively. The analysis was conducted at a flow rate of 1.5 ml/min. Then, assuming that the peak area of EGCG-C16 in the unreacted reaction solution was 100%, the ratio of the peak area of EGCG-C16 in the reaction solution after a lapse of the predetermined time was determined as a remaining ratio (%) of EGCG-C16. As Comparative Example 7, the same treatment was carried out using EGCG to which no acyl group was introduced, instead of the EGCG derivatives. The results thereof are shown in FIG. 4. FIG. 4 is a graph showing the relationship between the reaction time of EGCG-C16 and the remaining ratio of EGCG-C16. In FIG. 4, "D-ring" indicates the D-ring derivative, and the "B-ring" indicates the B-ring derivative.

As can be seen from FIG. 4, after a lapse of 24 minutes, the peak area of the D-ring derivative was reduced to 0.5% of that at the start of the reaction, whereas the remaining ratio of the B-ring derivative was 44%. Thus, it was found that the B-ring derivative exhibits higher metabolic stability than the D-ring derivative.

INDUSTRIAL APPLICABILITY

According to the present invention, it is possible to inhibit bacterial infection with excellent stability and antibacterial properties. Moreover, in the antibacterial agent of the present invention, EGCG as the basic skeleton of the EGCG derivative is, for example, catechin contained in tea and the like, and it is well known that catechin is excellent in safety. Also, the acyl group(s) of $R^1$ to $R^6$ of the EGCG derivative is excellent in safety. Therefore, it can be said that the antibacterial agent of the present invention is a pharmaceutical composition that also has excellent safety.

The invention claimed is:
1. A method for inhibiting bacterial infection by *S. aureus*, the method comprising:
administering an epigallocatechin gallate derivative represented by the following chemical formula (1), an isomer thereof, or a salt thereof, wherein the isomer is a tautomer, a stereoisomer or an optical isomer:

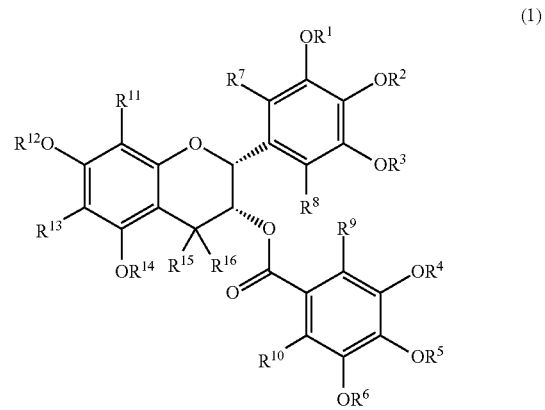

(1)

where:
R$^1$ to R$^6$ are each a hydrogen atom, halogen, sodium, potassium, or an acyl group and may be identical to or different from one another,
wherein the acyl group has the following chemical formula (2):

—C(O)R$^{17}$  (2), where R$^{17}$ is a straight or branched, saturated or unsaturated hydrocarbon chain that includes a carbon number of 1 to 19, and may be substituted with one or more substituents, wherein the one or more substituents are independently selected from the group consisting of an alkyl group, amino group, an alkylamino group or a dialkylamino group,
wherein
at least one of R$^1$ to R$^6$ is the acyl group, where R$^{17}$ of the acyl group of the at least one of R$^1$ to R$^6$ is an unsaturated hydrocarbon chain;
R$^{12}$ and R$^{14}$ are a hydrogen atom, halogen, sodium, or potassium and may be identical to or different from one another; and
R$^7$ to R$^{11}$, R$^{13}$, R$^{15}$, and R$^{16}$ are each a hydrogen atom.

2. The method according to claim 1, wherein
the alkyl group is a straight-chain or branched alkyl group having 1 to 6 carbon atoms,
an alkyl group in the alkylamino group is a straight-chain or branched alkyl group having 1 to 6 carbon atoms,
an alkyl group in the dialkylamino group is a straight-chain or branched alkyl group having 1 to 6 carbon atoms, and
R$^1$ to R$^6$ may be identical to or different from one another.

3. The method according to claim 1, wherein
the alkyl group is a methyl group,
the alkylamino group is a methylamino group,
the dialkylamino group is a dimethylamino group, and
R$^1$ to R$^6$ may be identical to or different from one another.

4. The method according to claim 1, wherein at least one of R$^1$, R$^2$, R$^5$, and R$^6$ is the acyl group.

5. The method according to claim 1, wherein at least one of R$^1$, R$^2$, R$^5$, and R$^6$ is the acyl group, and the rest are each a hydrogen atom.

6. The method according to claim 1, wherein R$^{12}$ and R$^{14}$ are a hydrogen atom.

7. The method according to claim 1, wherein the number of carbon atoms in R$^{17}$ in the acyl group is 12 to 18.

8. The method according to claim 1, wherein R$^{17}$ in the acyl group is at least one of a saturated straight hydrocarbon-chain and an unsaturated straight hydrocarbon-chain.

9. The method according to claim 1, wherein the acyl group is at least one acyl group selected from the group consisting of a butyryl group, an octanoyl group, a trans-8-methyl-6-nonenoyl group, a geranoyl group, a lauroyl group, 12-(dimethylamino)lauroyl group, a farnesoyl group, a palmitoyl group, a palmitoleyl group, a stearoyl group, an oleoyl group, a linoleyl group, a linolenyl group, an eicosanoyl group, and isomers thereof, wherein the isomers are tautomers, stereoisomers or optical isomers.

* * * * *